(12) United States Patent
Krietzman et al.

(10) Patent No.: US 12,097,384 B2
(45) Date of Patent: Sep. 24, 2024

(54) ENERGY AND GASEOUS HEALTH SUPPLEMENTS

(71) Applicants: Mark H. Krietzman, Palos Verdes, CA (US); Renz Wolfgang, Rheinfelden (DE)

(72) Inventors: Mark H. Krietzman, Rancho Palos Verdes, CA (US); Wolfgang Renz, Rheinfelden (DE)

(*) Notice: Subject to any disclaimer, the term of this patent is extended or adjusted under 35 U.S.C. 154(b) by 0 days.

(21) Appl. No.: 18/017,652

(22) PCT Filed: Mar. 11, 2022

(86) PCT No.: PCT/US2022/020058
§ 371 (c)(1),
(2) Date: Jan. 23, 2023

(87) PCT Pub. No.: WO2022/197561
PCT Pub. Date: Sep. 22, 2022

(65) Prior Publication Data
US 2023/0381535 A1    Nov. 30, 2023

Related U.S. Application Data

(60) Provisional application No. 63/161,782, filed on Mar. 16, 2021, provisional application No. 63/161,801, filed on Mar. 16, 2021.

(51) Int. Cl.
*A61N 5/06*    (2006.01)

(52) U.S. Cl.
CPC ...... *A61N 5/062* (2013.01); *A61N 2005/0605* (2013.01); *A61N 2005/0626* (2013.01)

(58) Field of Classification Search
CPC .............. A61N 5/06; A61N 2005/0605; A61N 5/0613; A61N 5/062; A61N 5/0622;
(Continued)

(56) References Cited

U.S. PATENT DOCUMENTS

| 6,682,472 B1 * | 1/2004 | Davis ..................... A61B 5/128 |
| | | 381/313 |
| 9,084,440 B2 | 7/2015 | Zuber et al. |

(Continued)

FOREIGN PATENT DOCUMENTS

| CN | 1541577 | 11/2004 |
| CN | 101518361 | 9/2009 |

(Continued)

OTHER PUBLICATIONS

International Patent Application No. PCT/US2022/020058; Int'l Search Report; dated Jul. 1, 2022; 4 pages.

(Continued)

*Primary Examiner* — Ahmed M Farah
(74) *Attorney, Agent, or Firm* — Mark H. Krietzman

(57) ABSTRACT

Disclosed herein are method to deliver supplemental or therapeutically effective aliquots or doses of one or more of at least gaseous fluids to at least one of the ear canal, eyes, skin, hair and lungs. Methods and systems may include delivery of energy aliquots of photodynamic energy including in the red, long red and/or near IR spectra to the eyes. The method may include delivering gaseous fluid to a subject in an enclosed space with a partially opened bottom and a vent opposite the bottom, providing a gaseous fluid douche or bath to at least one of the eyes, ears, skin, hairline, nose and mouth of the subject.

7 Claims, 15 Drawing Sheets

(58) Field of Classification Search
CPC .... A61N 2005/0626; A61N 2005/0643; A61N 2005/065; A61N 2005/0647; A61N 2005/0659; A61N 2005/0662; A61N 2005/0663; A61B 5/12; A61B 5/121; A61B 5/125; A61B 5/128
USPC .............................. 607/88–91, 100, 136, 137
See application file for complete search history.

(56) References Cited

U.S. PATENT DOCUMENTS

| | | |
|---|---|---|
| 9,510,623 B2 | 12/2016 | Tucker et al. |
| 11,033,056 B2 | 6/2021 | Gill et al. |
| 2012/0328711 A1 | 12/2012 | Huang et al. |
| 2020/0155483 A1 | 5/2020 | Djalilian |
| 2020/0338349 A1* | 10/2020 | Djalilian ............ A61N 1/36038 |
| 2020/0384287 A1* | 12/2020 | Hetz ................... A61N 5/0613 |
| 2022/0161054 A1* | 5/2022 | Drinan ................... A61K 35/28 |
| 2023/0232886 A1 | 7/2023 | Robinson et al. |

FOREIGN PATENT DOCUMENTS

| | | |
|---|---|---|
| CN | 101606758 | 12/2009 |
| CN | 201379072 | 1/2010 |
| CN | 108721787 A | 11/2018 |
| CN | 111388851 A | 7/2020 |
| DE | 102018000237 A1 | 7/2019 |
| JP | 3164992 | 12/2010 |
| JP | 03228934 U | 11/2020 |
| WO | WO-2022197561 A1 * | 9/2022 |

OTHER PUBLICATIONS

International Patent Application No. PCT/US2022/020058; Int'l Written Opinion; dated Jul. 1, 2022; 7 pages.

* cited by examiner

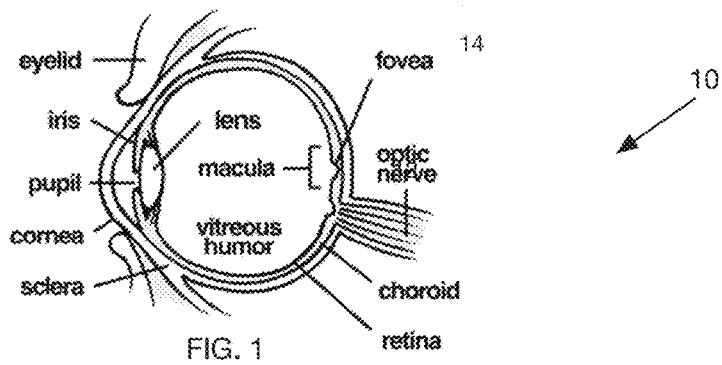
FIG. 1
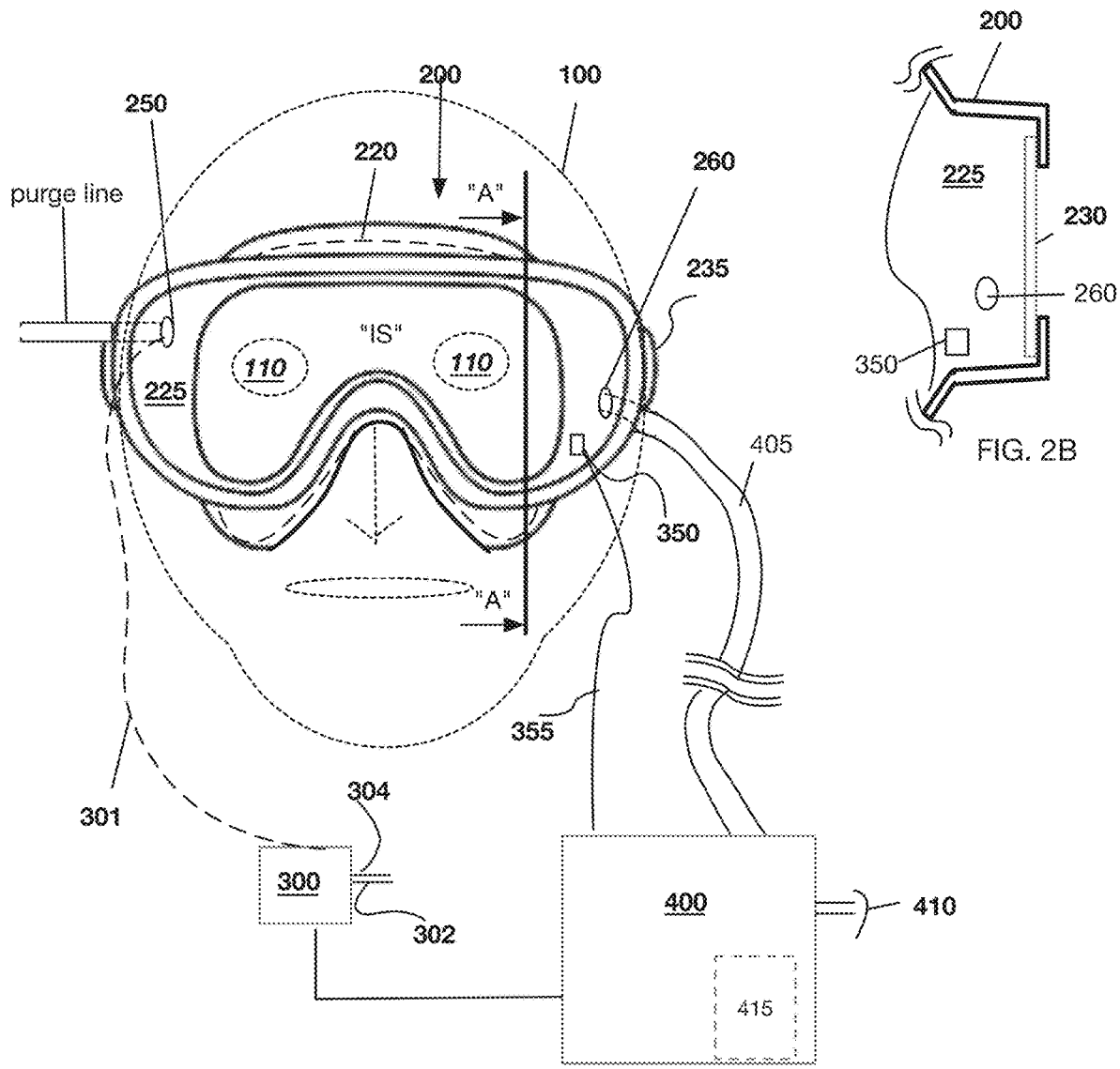
FIG. 2A
FIG. 2B

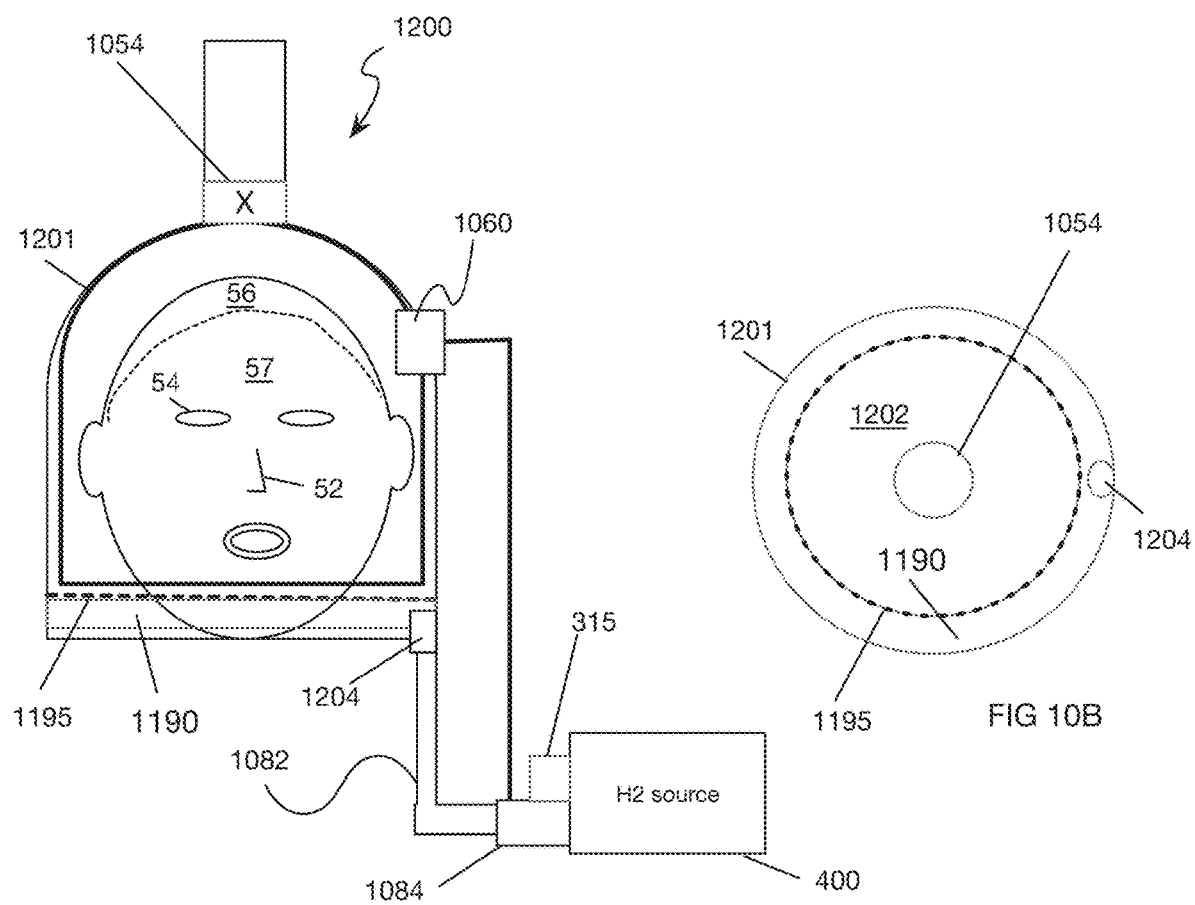
FIG. 10A
FIG 10B
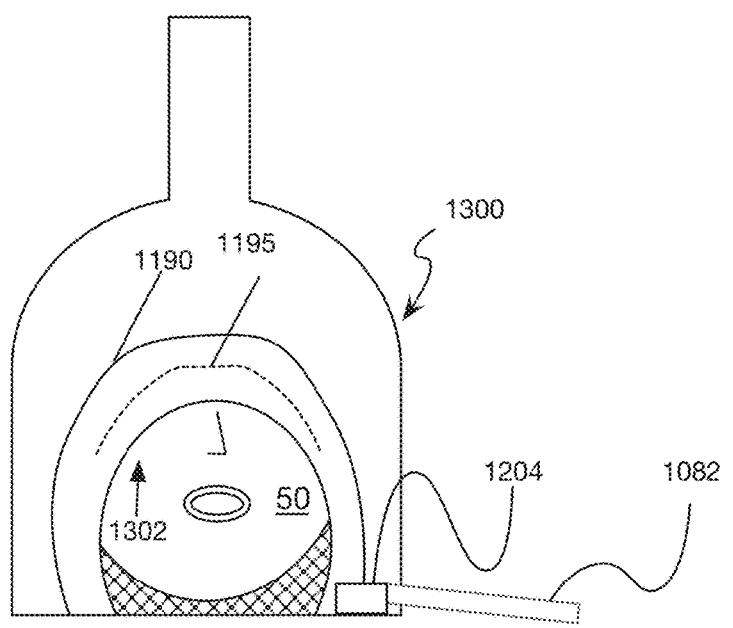
FIG 11

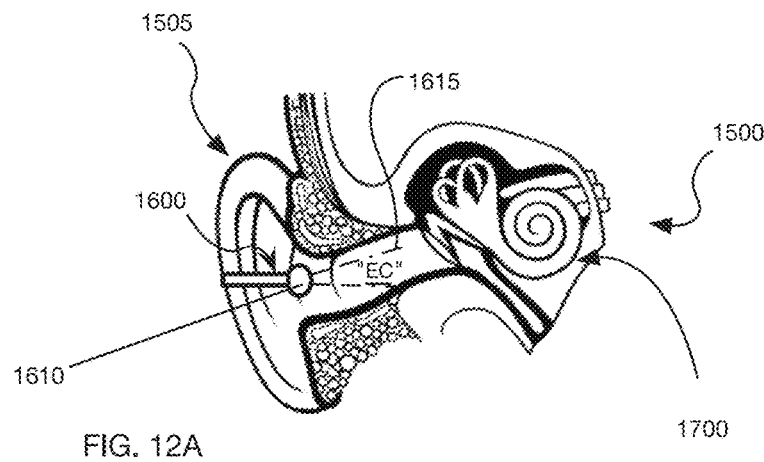
FIG. 12A
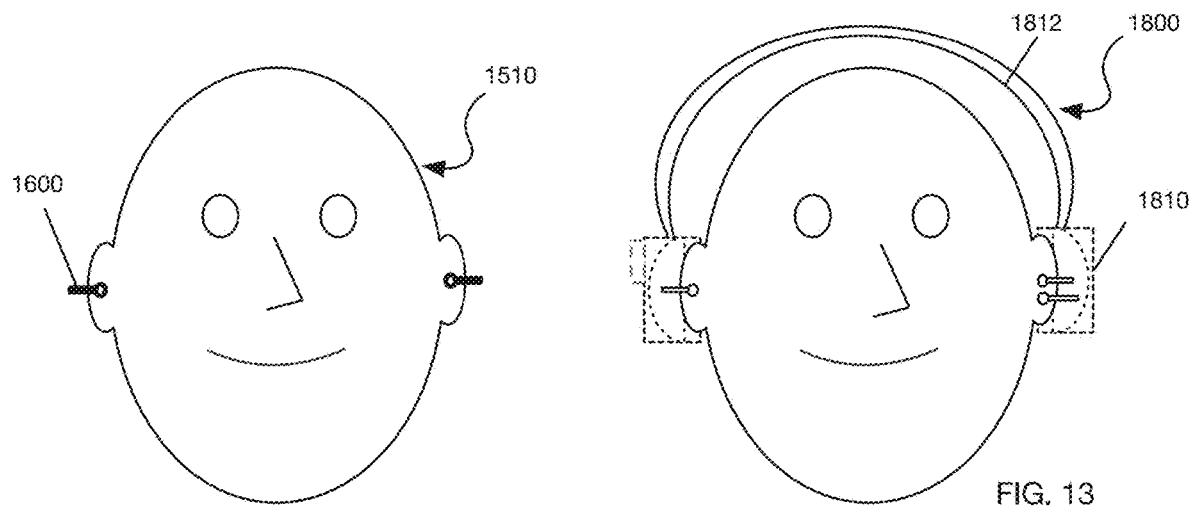
FIG. 12B
FIG. 13
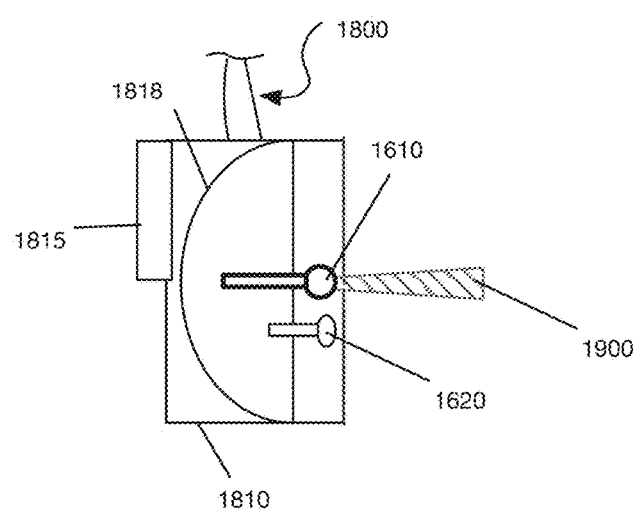
FIG. 14

ENERGY AND GASEOUS HEALTH SUPPLEMENTS

CROSS-REFERENCE TO RELATED APPLICATION

The present application is a 371 National Stage of International Patent Application No. PCT/US2022/020058, filed Mar. 11, 2022, which claims priority to United States ("U.S.") provisional patent application 63/161782 filed Mar. 16, 2021 and United States ("U.S.") provisional patent application filed 63/161,801 filed Mar. 16, 2021 both of which are hereby incorporated by this reference as if fully set forth herein.

FIELD OF THE DISCLOSURE

The present disclosure relates generally to ontological and ocular supplements.

BACKGROUND

Vision and/or hearing decline is a serious quality of life and health problem which leads to additional health issues.

A non-exhaustive list of those include but are not limited to correlation between cognitive decline and vision decline. Loss of vision and cognition often coincide. Research funded by the National Eye Institute (NEI) and the National Institute on Aging (NIA) have found that vision loss precedes loss of mental capacity. In a population-based sample of older US adults, visual impairment measured at distance is associated with declining cognitive, Worsening vision in older adults may be adversely associated with future cognitive functioning. Maintaining good vision may be an important interventional strategy for mitigating age-related cognitive declines.

Age-related macular degeneration (AMD) both wet and dry AMD can harm the sharp, central vision needed to see objects clearly AMD (dry) is a degenerative process of the central area of the retina, the macula, causing a subsequent loss of function of the overlying photoreceptor cells; can cause complete loss of central vision and legal blindness. AMD wet; is caused by abnormal blood vessel growth and leakage of blood and fluid beneath the central area of the retina, the macula, often in response to the damage done from dry AMD; can cause complete loss of central vision (more devastating than in dry AMD) and legal blindness. Ocular diseases also include cataract, glaucoma, retinitis pigmentosa, diabetic retinopathy (DR) and these have been shown to correlate to reactive oxygen species (ROS).

A Johns Hopkins study that tracked 639 adults for nearly 12 years, they found that mild hearing loss doubled dementia risk. Moderate loss tripled risk, and people with a severe hearing impairment were five times more likely to develop dementia.

The NIH (National Institute of Health) explains that tinnitus is commonly described as a ringing in the ears, but it also can sound like roaring, clicking, hissing, or buzzing. It may be soft or loud, high pitched or low pitched. You might hear it in either one or both ears.

Tinnitus is not in and of itself a disease, rather it is a symptom that something is wrong in the auditory system, which includes the ear, the auditory nerve that connects the inner ear to the brain, and the parts of the brain that process sound. Something as simple as a piece of earwax blocking the ear canal can cause tinnitus. But it can also be the result of a number of health conditions.

People who work in noisy environments—such as factory or construction workers, road crews, or even musicians—can develop tinnitus over time when ongoing exposure to noise damages tiny sensory hair cells in the inner ear that help transmit sound to the brain. This is called noise-induced hearing loss.

Service members exposed to bomb blasts can develop tinnitus if the shock wave of the explosion squeezes the skull and damages brain tissue in areas that help process sound. In fact, tinnitus is one of the most common service-related disabilities among veterans returning from Iraq and Afghanistan.

Even with all of these associated conditions and causes, some people develop tinnitus for no obvious reason. Most of the time, tinnitus isn't a sign of a serious health problem, although if it's loud or doesn't go away, it can cause fatigue, depression, anxiety, and problems with memory and concentration. For some, tinnitus can be a source of real mental and emotional anguish.

As the inner ear is constantly using energy, blood supply to the ear is particularly important. Controlling this blood supply relies on how well individual cells in a blood vessel can contract and relax to change its width, as this determines how much blood reaches the inner ear. There is evidence that conditions such as diabetes, and, more generally, ageing, damage blood vessels and disrupt the control of blood flow to the ear, which may lead to hearing loss. Exposure to loud noise can impair cochlear microcirculation and cause noise-induced hearing loss. TNF-α signaling has been shown to be activated in such loss and to control artery vasoconstriction that regulates cochlear microcirculation.

It is therefore a desideratum to provide supplements and modalities, which may be combinatorial for vision and hearing.

DISCLOSURE

Disclosed herein are supplement or nutraceutical doses of compounds including applying aliquots of photodynamic light and/or a aliquots of gaseous fluids including but not limited to oxygen, hydrogen, oxyhydrogen and nitrogen to the eyes and ears. In other instances, disclosed herein are pharmaceutical doses of effective compounds including applying aliquots of photodynamic light and/or a aliquots of gaseous fluids including but not limited to oxygen, hydrogen, oxyhydrogen and nitrogen to the eyes and ears.

Disclosures are for supplements to help maintain homeostasis for the cochlear microcirculation which may also reduce instances of tinnitus, limit, reverse or slow down hearing degradation and onset of dementia.

In some instances the supplement is a locally effective dose or aliquot of energy (EDE) in an ear canal increasing circulation in the cochlea vasculature and increasing nitric oxide in the local area adjacent to the cochlea and wherein vasodilation increases in the cochlear microvasculature. A supplement of gaseous hydrogen or oxyhydrogen for the ear canal can be taken before, during and after applying the EDE.

In some instances device and methods provide gaseous supplements which may increase one or more of circulation, increase nitric oxide, reducing oxidative stress, inflammation, and autophagic stress in the cochlea vasculature and/or in the local area adjacent to the cochlea.

FIG. 1 shows an overview of the human eye 10. The macula 12 and fovea 14 are regions which are most impacted by AMD.

The present disclosure provides, at least in part, a device and system utilizing light provided by one of a LASER and Light emitting Diode (LED) at one or more predetermined wavelengths. In some instances a sensor or light receiver is an input to a controller which controls the application of one or more of the quantity of photons, wavelength and amount of energy in an aliquot/dose. Emissions of Long Red and Near-Infrared may be referred to collectively as Red Bio-active light (RBL). Red may be called long red within a spectrum of >625 nms to <700 nms with peak wavelengths >640-670 nm and Near-Infrared typical ranges from >700 nms and <1400 nm (with typical peak wavelengths: 850 nm, 940 nm, 1064 nm). Those of ordinary skill in the art and the skilled artisan will recognize variation is narrow and does not create substantial uncertainty in the terms. Hence the terminology RBL is encompasses the entirety of both long red and near-infrared.

In some instances red in non-visible region also referred to as near infrared may be used simultaneously or through a rapid switching mode with RBL. The light modes may be applied in doses or aliquots based on a lookup table or sensor data or other inputs to the control systems. Such light may be used as a health supplement based controls systems. Application of light may also be one of applied via a preset timing control, a predetermined algorithm and/or via a dynamic control system controlled, at least in part, by physiological measures of the user including but not limited to data harvested from sensors associated with or information about users via one or more of physiological sensors including but not limited to measurements of temperature, heart rate, blood pressure, temperature, skin response, O2 saturation and/or user feedback.

The present disclosure provides aspects of devices, methods and systems to deliver one of an amount, a supplement of a gaseous fluid to an enclosed space "IS" forming a fluid douche or bath to the eyes. Wherein the gaseous fluid is at least one of oxyhydrogen, oxygen and hydrogen. In some instances the fluid is supplied to the IS in intervals with purge intervals between the gaseous fluid delivery intervals. In some instances the system and method supply different gaseous fluids sequential during different intervals.

In some instance the present disclosure provides aspects of devices, methods and systems to deliver one of an amount, a therapeutically effective aliquot of a gaseous fluid to an enclosed space "IS" forming a fluid douche or bath to the eyes. Wherein the gaseous fluid is at least one of oxyhydrogen, oxygen and hydrogen. In some instances the fluid is supplied to the IS in intervals with purge intervals between the gaseous fluid delivery intervals. In some instances the system and method supply different gaseous fluids sequential during different intervals.

In some instances the supplement fluid is supplied in intervals with purge intervals between the gaseous fluid delivery intervals. A controller in signal communications with a means to provide said gaseous fluid (means include but are not limited to a HHO generator, one or more storage tanks of at least one of N2, H2, O2 and HHO) and said controller maintains a volume of gaseous fluid at a predetermined pressure within the enclosed space "IS". In some instances the system and method supply different gaseous fluids sequential during different intervals. In some instance a nasal or nose cover is in fluid communication with the IS and the device further comprises at least a way valve through the side of the device which allows exterior air flow into the device. In some instances a nasal inhalation may be used to purge the device. In some instances the nasal inhalation directs the fluid to lungs and thereby biologically filters the IS fluid.

The present disclosure provides aspects of devices, methods and systems to deliver one of an amount, a supplement and a therapeutically effective aliquot of a gaseous fluid and photodynamic energy to an enclosed space "IS" forming a fluid douche or bath to the eyes. Wherein the gaseous fluid is at least one of oxyhydrogen, oxygen and hydrogen. In some instances the fluid is supplied in intervals with purge intervals between the gaseous fluid delivery intervals. A controller in signal communications with a means to provide said gaseous fluid (means include but are not limited to a HHO generator, one or more storage tanks of at least one of N2, H2, O2 and HHO) and said controller maintains a volume of gaseous fluid at a predetermined pressure within the enclosed space "IS". In some instances the system and method supply different gaseous fluids sequential during different intervals. In some instance a nasal or nose cover is in fluid communication with the IS and the device further comprises at least a way valve through the side of the device which allows exterior air flow into the device. In some instances lasers or LEDS are mounted on the device facing inward, are in signal communication with a power supply and are configured to produce aliquots of light for at least one of red, long red and near IR. In some instances the aliquots of light in predetermined spectra produced by the LEDs, which are in signal communication with the controller or a second controller, are controlled by the controller and the light may be applied in partial allocations via intervals or light may be sequenced with or between intervals of fluid delivery.

The device light energy delivery controller receives sensor information from sensor which measures the energy delivered to the IS during an interval and the controller at least one of increase and decrease the photonic output of the LEDS based on said sensor information. The controller may receive sensor information from sensor which measures the energy delivered to the IS during an interval and the controller one of stop the LED output and continues the LED output based on said sensor information. In some instances a nasal inhalation may be used to purge the device. In some instances the nasal inhalation directs the fluid to lungs and thereby biologically filters the IS fluid.

The present disclosure provides aspects of devices, methods and systems to deliver an aliquot of photodynamic energy to an enclosed space "IS" one of lasers and LEDs are mounted on the device facing inward are in signal communication with a power supply to produce aliquots of light for at least one of red, long red and near IR. The aliquots of light in predetermined spectra produced by the LEDs are in signal communication with a controller and the light may be applied in partial allocations via intervals. At least one sensor may be in signal communication with the controller whereby the photodynamic energy, energy or spectra of light over time is measured and said measurement is supplied to the controller which is configured to adjust the light output at least based in part on sensor data.

The present disclosure provides aspects of devices, methods and systems to deliver therapeutically effective treatment for relief for tinnitus, the method including directing at least one locally effective dose or aliquot of energy (EDE) into an ear canal; one or more of increasing circulation in the cochlea vasculature and increasing nitric oxide in the local area adjacent to the cochlea; and wherein vasodilation increases in the cochlear microvasculature. In some instances the EDE is at least one of red light, long red light, near IR light and blue light. In some instances the light is delivered via sequential modes adjusted by a controller. In some instances one or more sensors provide input to the controller for adjustment of mode, frequency, duration and intensity. In some instances one or more sensors provide at least one of sampling, and measurement of at least one of loudness, decibels, temperature, pressure, vibration provides a one or more sensors provide input to the controller for adjustment of mode, frequency, duration and intensity.

The present disclosure provides aspects of devices, methods and systems to deliver a therapeutically effective aliquot of at least two modes of photodynamic energy to the inner ear or ear canal of a subject including directing at least two locally effective dose or aliquot of energy (EDE) into an ear canal; at least one mode being blue light in the circadian stimulating range; at least one mode being RBL; wherein the modes of light at least one of increases circulation in the cochlea vasculature, increase nitric oxide in the area adjacent to the cochlea, and alters the circadian cycle of the subject. In some instances the EDE is at least one of red light, long red light, near IR light and blue light. In some instances the light is delivered via sequential modes adjusted by a controller. In some instances one or more sensors provide input to the controller for adjustment of mode, frequency, duration and intensity. In some instances one or more sensors provide at least one of sampling, and measurement of at least one of loudness, decibels, temperature, pressure, vibration provides a one or more sensors provide input to the controller for adjustment of mode, frequency, duration and intensity.

The present disclosure provides, at least in part, as part of a combinatorial approach which may or may not include compositions comprising at least one vasodilator and a carrier agent. In other instances at least one of intravenous injection of gelatin and corticosteroid to improve transport of fluids without increasing pressure within the cochlear microcirculatory system.

The microprocessors, controllers, computing devices/smart devices disclosed herein operate with memory and processors whereby code is executed during processes to transform data, the computing devices run on a processor (such as, for example, controller or other processor that is not shown) which may include a central processing unit ("CPU"), digital signal processor ("DSP"), application specific integrated circuit ("ASIC"), field programmable gate array ("FPGA"), microprocessor, etc. control may include pulse width modulation "PWM". Alternatively, portions DCA devices may also be or include hardware devices such as logic circuitry, a CPU, a DSP, ASIC, FPGA, etc. and may include hardware and software capable of receiving and sending information. The electronic board, printed circuit board (PCB) contains at least a microprocessor, inputs and output and memory. It may contain a communication chipset (blue tooth, near field and the like) or a wired input output connection whereby the quantity, amount, molar ratio, pressure, temperature and duration of fluid exposure and the light and energy emitting device can be recorded and/or reported for analysis and to confirm use, treatment period and/or compliance with treatment regimes. Reporting of collected data may be via a cellular network or other internet connection as known in the art.

By "combination" or "in combination with," are not intended to imply that the therapy or the therapeutic agents must be administered at the same time and/or formulated for delivery together (e.g., in the same composition), although these methods of delivery are within the scope described herein. It will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In some embodiments, a combination includes a formulation of a first and a second therapeutic agent, with or without instructions for combined use or to combination products. The combined compounds can be manufactured and/or formulated by the same or different manufacturers. The combination partners may thus be entirely separate pharmaceutical dosage forms or pharmaceutical compositions that are also sold independently of each other. The kit may include a device to apply at least an effective dose or concentration of energy to cause a biological effect in mammals. In some embodiments, instructions for their combined use are provided: (i) prior to release to practitioners (e.g. in the case of a "kit of part" comprising the compound of the disclosure and the other therapeutic agent); (ii) by the practitioners themselves (or under the guidance of a physician) shortly before administration; (iii) the patient themselves by a practitioners, physician or medical staff.

DRAWINGS

The disclosure may be better understood by referring to the following figures. The components in the figures are not necessarily to scale, emphasis instead being placed upon illustrating the principles of the invention. In the figures, like reference numerals designate corresponding parts throughout the different views.

FIG. 1 is an overview of eye;

FIG. 2A is a user representation wearing a fluid delivery device to deliver aliquots of at least one fluid to the eyes of a subject.

FIG. 2B is a partial cross section of FIG. 2A along line A-A.

FIGS. 9A and 9B show a low pressure gaseous fluid delivery and collection system.

FIGS. 10A and 10B shows a low pressure gaseous fluid delivery and collection system.

FIG. 11 shows a low pressure gaseous fluid delivery and collection system.

FIG. 12A is an overview of ear anatomy and a disclosed energy device and method to deliver aliquots of energy;

FIG. 12B is a representation of an energy delivery device to deliver aliquots of energy of the disclosure positioned on a subject/user.

FIG. 13 is an overview of a wearable energy delivery and feedback device of the disclosure.

FIG. 14 is a component view of aspects of a wearable energy delivery and feedback device of the disclosure.

In the Figures, like reference numerals designate corresponding parts throughout the different views. All callouts and annotations are hereby incorporated by this reference as if fully set forth herein. All cited references are hereby incorporate by this reference as if fully set forth herein.

Figure 2D:
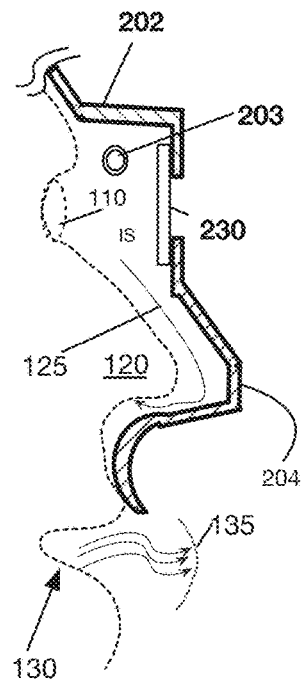
FIG. 2D is a partial cross section of FIG. 2C along line B-AB.

It will be understood that various aspects or details of the invention may be changed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

FURTHER DISCLOSURE

Disclosed herein are devices, supplement compositions, cocktail supplements of energy and gas, including but not limited to light (photodynamic) and local fluid topical. The supplements may be combined or applied separately to.

Supplying exogenous antioxidants to suppress the progression of ocular pathologies and alleviate the eyes from oxidative injury have been shown to provide some efficacy.

Hydrogen: $H_2$ has been shown to be an anti-inflammatory. $H_2$ has been shown to decrease the expression of a number of pro-inflammatory factors, including at least tumor necrosis factor-α (TNF-α), interleukin (IL)-6, IL1β, IL-10, IL-12, chemokine ligand 2 (CCL2. Furthermore, $H_2$-rich saline reduced serum diamine oxidase, TNF-α, IL-1βIL-6, tissue malondialdehyde, protein carbonyl and myeloperoxidase activity, and also inhibited pro-apoptotic players, including JNK and caspase-3.

It has been reported that $H_2$ gas inhalation has significantly reduced the number of total cells, eosinophils and lymphocytes in the bronchial alveolar lavage fluid, and increased the level of IL-4, IL-13, TNF-α and chemokine (C-X-C motif) ligand 15. The IL-4 serum level was significantly decreased following inhalation. $H_2$ gas inhalation markedly upregulated the activity of superoxide dismutase and significantly attenuated the increased level of malondialdehyde and myeloperoxidase in allergic asthmatic mice. Hydrogen gas has been shown in animal models to reduce concentrations of IL-4, IL-13 and TNF-α.

A mixed gas consisting of about 65% $H_2$ and about 35% $O_2$ is disclosed. In other instances mixtures ranging from about 50% $H_2$ to about 85% $H_2$ may be used. In some instances the ration may be about 80% hydrogen and about 20% oxygen. Local or topical exposure to a fluid rich in $H_2$ may be combined with modalities including but not limited to photodynamic exposures of defined aliquots of light and/or sequenced additional fluids applied topically or locally.

Hydrogen rich saline has been shown in animal studies to reduce retinal damage from light exposure even if administered post exposure. It has been reported in animal studies of rabbits that the effects of ROS are wide-ranging, but three reactions are particularly relevant to cell injury: lipid peroxidation of membranes, oxidative modification of proteins, and oxidative damage to DNA. This study shows that the treatment of alkali-injured corneas with $H_2$ solution highly suppressed oxidative stress in the cornea. The authors noted that "$H_2$ rapidly diffuses into tissues and cells, and it is not mild enough either to disturb metabolic redox reactions or to affect ROS that function in cell signaling. $H_2$ is an inert gas and only the strong oxidants, for example, hydroxyl radicals and peroxynitrite, are able to oxidize it. In other words $H_2$ reacts with strong oxidants such as hydroxyl radical and peroxynitrite in cells, and thus it is a potent agent for preventive and therapeutic antioxidant applications. $H_2$ can be consumed in the human body by various ways, including inhaling $H_2$, drinking hydrogen water ($H_2$-dissolved water), taking a hydrogen bath, injecting $H_2$-dissolved saline, dropping $H_2$ onto the eye". Hydrogen has been shown to have no adverse effects and great efficacy on nearly all pathogenic states involved in oxidative stress and inflammation.

Further hydrogen has been shown to reduce stress. "Molecular hydrogen increases resilience to stress in mice". Molecular hydrogen increases resilience to stress in mice.

Recent studies indicate that photodynamic of doses of red and near-IR: Red may be called long red within a spectrum of >625 nms to <700 nms with peak wavelengths >640-670 nm and Near-Infrared typical ranges from >700 nms and <1400 nm (with typical peak wavelengths: 850 nm, 940 nm, 1064 nm) affect bio-physiological functions and are also described herein as "bioactive" they may improve eye health, skin health, hair growth, and cognitive function. Emissions of Long Red and Near-Infrared may be referred to collectively as Red Bioactive light (RBL). Those of ordinary skill in the art and the skilled artisan will recognize variation is narrow and does not create substantial uncertainty in the terms. Hence the terminology RBL is encompasses the entirety of both long red and near-infrared.

IR LED treatment can penetrate the skin between 5 and 10 mm and has been used to treat wounds, ulcers, recalcitrant lesions, and cutaneous scleroderma. Simulations using LEDs have been carried out for a range of beam widths in the range 1 to 40 mm. The results show that as the beam width is increased there is an increase in the depth of penetration, which can clearly be seen by the use of intensity contours, each representing a 1% fraction of the maximum intensity. The 1% fraction contours were chosen after experimentation with other values for penetration such as $1/e$ and $1/e^2$ for a clear and clean graphical representation of the photo-distribution matrix. It is shown that the beam divergence as the light passes through the skin model.

"Bioactive Exposure" refers to directing RBL at at least one of a biological system which may be a specific organ or any part of the body.

Disclosed herein are additional methods and systems to provide Bioactive Exposure as one of a supplement and therapeutic dose to:

A. As a cocktail or sequenced combinatorial therapy/therapies for vision and ocular health.

B. As a cocktail or sequenced combinatorial therapy/therapies to ameliorate or postpone the onset or worsening symptoms of AMD.

C. As a cocktail or sequenced combinatorial therapy/therapies to reduce ROS and their impact on ocular health.

D. As a cocktail or sequenced combinatorial therapy/therapies to ameliorate or stave off the onset or worsening symptoms of cognitive decline associated with vison decline.

Red and red in the near infrared spectrum has been used clinically for many years in the context of wound healing, plastic surgery, chronic joint pain and in the field of dermatology. Many of the effects of such light are related to observed effects on blood flow and angiogenesis, which are driven at least in part through nitric oxide dependent processes. Such light stimulates release of an endothelium dependent vasodilator and rescues vascular dysfunction in a diabetes model.

Application of light may also be one of applied via a predetermined algorithm or via a dynamic control system controlled, at least in part, by physiological measures of the user including but not limited to data harvested from sensors associated with or information about users, such as one or more of physiological sensors including but not limited to temperature, O2 saturation, heart rate and blood pressure of user.

Disclosed herein are nonlimiting aspects of devices, systems, methods and compositions which can be included in a pharmaceutical, supplement or nutraceutical composition or a treatment regime together with additional active agents, carriers, vehicles, excipients, or auxiliary agents identifiable by a person skilled in the art upon reading of the present disclosure, and such compositions, methods, device and systems are within the scope of this disclosure. All publications cited herein are hereby incorporated by reference as if fully set forth herein.

The compositions may comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds and/or adjuvants can also be incorporated into the compositions. A pharmaceutical composition is formulated to be compatible with its intended route of administration. Examples of routes of administration include topical, local fluid douche or bath, local exposure to energy.

"Administration" as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell or organ encompasses contact of a reagent to same, as well as contact of a reagent to a fluid, where the fluid is in contact with same. "Administration" also means in vitro and ex vivo treatments, e.g., of a cell, by a reagent, diagnostic, binding compound, or by another cell. The term "subject" includes any organism, preferably an animal, more preferably a mammal (e.g., rat, mouse, primate, dog, cat, and rabbit) and most preferably a human.

A pharmaceutically effective dose (ED) or effective concentration (EC) is a dose or concentration of an element (such as hydrogen or oxygen) that produces a biological response. The term effective dose is used when measurements are taken in vivo, while the term effective concentration is used when the measurements are taken in vitro. This is generally defined by the range between the minimum effective dose (MED) and the maximum tolerated dose (MTD). The MED is defined as the lowest dose level of a pharmaceutical product that provides a clinically significant response in average efficacy, which is also statistically significantly superior to the response provided by the placebo. Similarly, the MTD is the highest possible but still tolerable dose level with respect to a pre-specified clinical limiting toxicity. In general, these limits refer to the average patient population.

An effective dose or aliquot of energy (EDE) or effective concentration of energy (ECE) of light (photons) or heat provided by such light to be bioactive, Bioactive includes but is not limited to the EDE or ECE to produce a biological response. The wavelength range of photodynamic bioactive light may change the EDE. The term EDE is used when measurements are taken in vivo, while the term effective concentration is used when the measurements are taken in vitro. This is generally defined by the range between the minimum effective energy dose (MEED) and the maximum tolerated dose (MTD).

In some instances a mammalian a subject to application of the EDE combined with at least on localized fluid therapy or supplement applied via a gaseous fluid supplied to a defined volume such as eye goggles with a facial seal.

FIG. 1 is an overview of gross anatomy of an eye 10. FIGS. 2A through 8 disclose devices and systems to deliver, provide, or otherwise administer the methods disclosed herein. FIG. 2A illustrates a user s head 100 who has placed an enclosed volume 200 over one or more eyes 110. The volume has one or more seals around an open perimeter 220 the seals seal against the user's face 120. The volume is generally a container open at the first end which interfaces with the face to close off the interior of the volume a scuba mask, swim goggles or the like are examples of such volumes. Suitable materials include but are not limited to HDPE (high density poly ethylene) polypropene and poly vinyl chloride. Materials should have very low permeability to hydrogen vapor at the pressures and temperatures being used.

In the instant disclosure the volume may be completely opaque or regions of it may be more transparent. There is a spectrum of opaqueness all of which is within the disclosure. In some instances the volume or goggle has an annular wall also referred to as a side wall 225 and that side wall is sealed against or formed as part of a generally front wall 230 (See generally FIG. 2B which is a partial cut-away of the goggle shown in FIG. 2A.) A strap or head band 235 is shown attached to each side of the volume and positioned to wrap around the user's head 100.

Disclosed herein are aspects of methods of delivering fluids to the eye 110 and systems and devices which illustrate aspects of the methods. A relief port or valve 250 fluidly connect from the enclosed space "IS" of the volume of fluid delivery system to the exterior "E". said valve 250 is configured to allow fluid to pass from the interior space to the exterior under conditions. The conditions may be fixed, variable or dynamically changing. A simple example is a pressure relief valve which is preset to allow fluid from the interior space which exceeds that preset pressure limit to evacuate or bleed out of the device. A more complex example would a manually adjustable pressure relief valve whereby the limit may be manually altered. A more complex valve would be an electronically controlled valve whereby the valve is in signal communication (via wire or wirelessly) 301 with a controller 300. The controller may have additional inputs 302/304 to receive data form sensors as part of the controller decisioning process. The controller is also in signal communications with the fluid distribution system 400. That fluid distribution includes at least one of a gaseous fluid compressed in a storage vessel, a pump to compress a gaseous fluid and a device to generate oxyhydrogen or brown's gas from liquid(s) in a predetermined stoichiometric mixture. The fluid distribution system is fluidly connected to the goggles via a transport hose 405 which fluidly connects to the goggles at an interface 260 whereby the gaseous fluid is transported to the google. The transport may be over a fixed interval or it may be over a variable interval. The valve (which may be one or more valves for redundancy) functions to normalize pressure in the goggles to a set limit. One or more pressure sensors or transducers 350 are affixed to or within the goggles to monitor pressure therein and changes in pressure therein. The controller receives input 355 from pressure sensor(s) 350 and one or more of turns on the flow of gaseous fluid, turns off the flow fluid, varies the flow rate of the gaseous fluid, varies the limit on the pressure relief valve 250, opens said valve, closes said valve to adjust for a target pressure limit. The purge valve can be connected to a purge line wherein the fluid inside the "IS" is purged with atmospheric air and vented via the purge line or removed via other filtration or scrubber. Those of ordinary skill in the art or the skilled artisan will recognize that multiple purge lines and/or multiple relief valves are within the scope of this disclosure. The "IS" is preferably less than 250 ml volume and more preferable less than 120 ml in volume, most preferably less than 80 ml in volume. The fluid distribution system is connected to a power supply 410 and/or has an internal power supply 415. The fluids transported include but are not limited to gaseous hydrogen, oxygen, atmospheric air and oxyhydrogen. The application of the fluid may be sequentially. For example hydrogen may be added via the system and method and it may be sequentially followed by another gaseous fluid such as oxygen or oxyhydrogen, or a purge fluid such as atmospheric air may intercede.

Figure 2C:
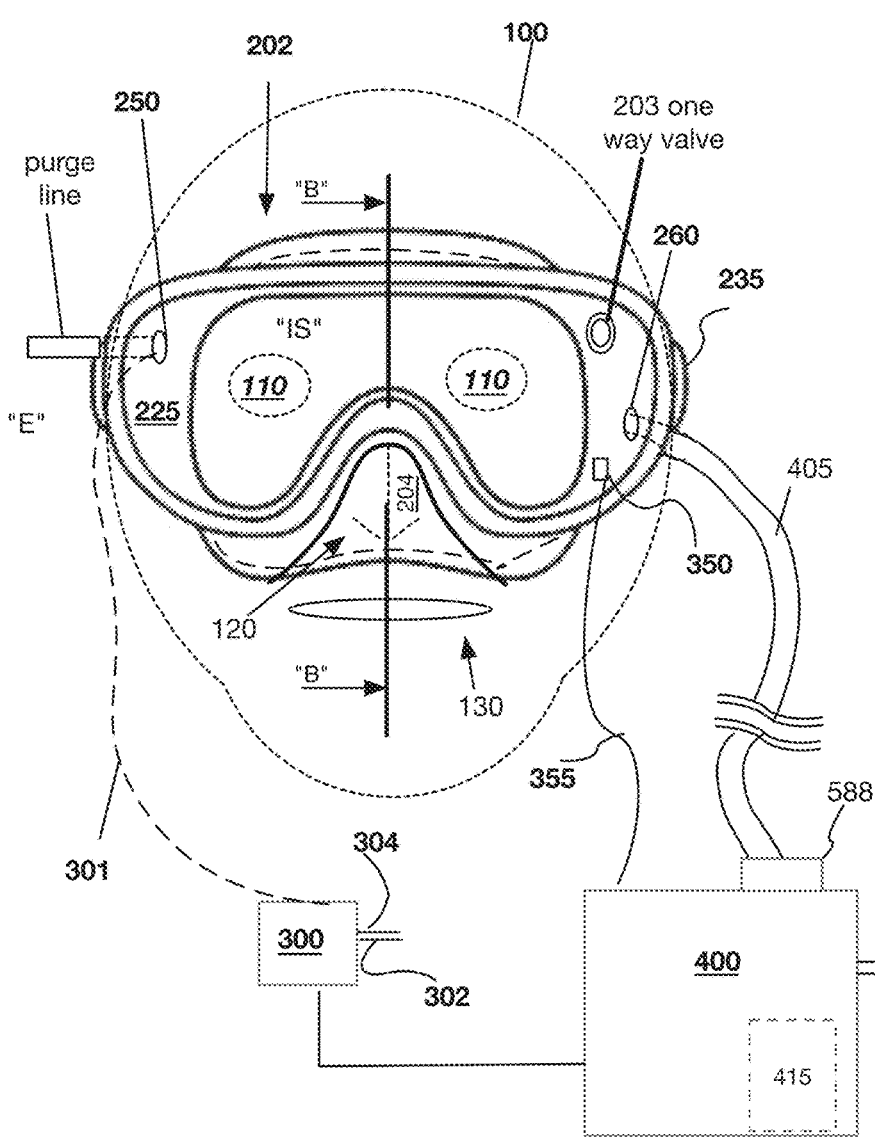
FIG. 2C is a biological purge system and method of a fluid delivery device to deliver aliquots of at least one fluid to the eyes of a subject.

FIGS. 2C and 2D illustrates a biological purge system and method of a fluid delivery device to deliver aliquots of at least one fluid to the eyes of a subject and reduce release of concentrated gas. The volume defining device or goggle 202 includes a nose cover 204 which covers a user's nose 120 and fluidly connects the IS with the nose. This system and device allows a user to also breath in the gaseous fluid being supplied. A one way valve 203 is in fluid communications with the exterior "E" configured for inflow of exterior air when a predetermined amount of negative pressure is in the IS. That inhaled atmospheric air is utilized as a purge gas, and is drawn in the nose 120 as the user inhales the volume in the IS. In other instances the supply hose is provided atmospheric air (or other fluid) and the user inhales that air supply via the nose without the need or use of a one way valve. An alert or alarm may be used to que the user as to when he/she needs to inhale. This method also supports inhalation of the gaseous fluid as a supplement or treatment. In some instances it is possible to provide a stream of HHO to the user, wherein the HHO can both be a topical for the eyes and an inhaled fluid for other uses. Each inhalation when the supply fluid is HHO will then have that dual function. The user also has the option to breath in from the mouth 130 to inhale atmospheric air.

This biological filtering of the gas in the IS is useful to periodically clear the IS. The user inhales the gaseous fluid in the IS along the lien of arrow 125 and after inhalation the gas is expelled with any other lung fluids along the line of arrows 135 via the user's mouth 130. The expelled fluids are a combination of gaseous fluids in the lungs from mouth 130 inhalation and gaseous fluid from the IS from nasal 120 inhalation and lack the concentration that any one of HHO, H2, N2 and O2 which may be supplied to the IS at higher than atmospheric air concentration would have. The system in some instances is configured to train, urge or alert the user to nasally purge periodically. After the user purges, the pressure sensor in signal communication with the controller one of an inside the goggle pressure sensor 350 or a pressure sensor 588 fluidly connected to the supply hose 405. The controller is configured to resupply the gaseous fluid to the IS post purge. Although a pressure relief valve and purge line may be provided, biological filtering can eliminate the need to release the IS to the exterior without biological filtering.

Figure 3:
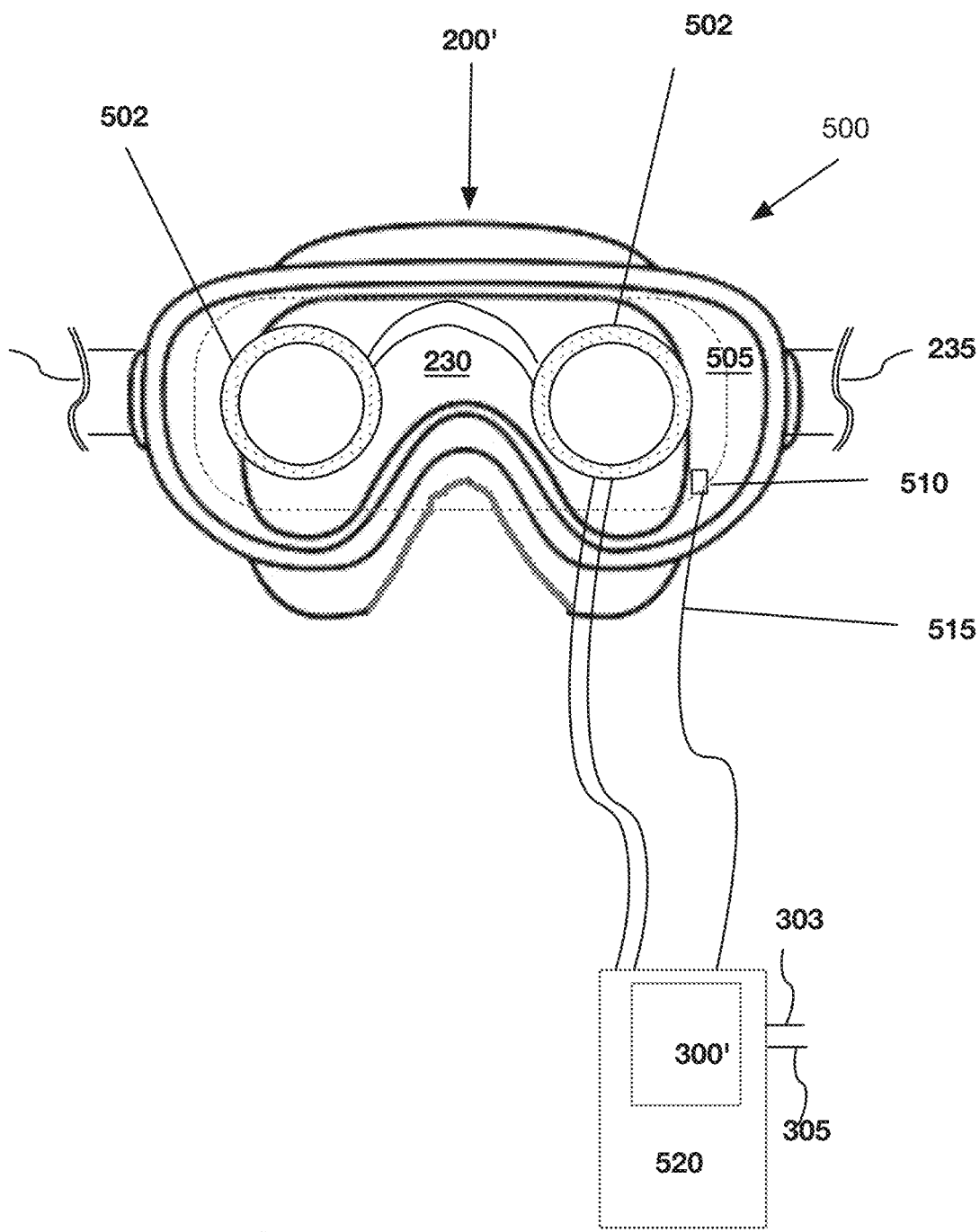
FIG. 3 is a representation of an energy delivery device to deliver aliquots of photodynamic energy to the eyes of a subject.

Disclosed herein are aspects of a system and method delivering aliquots of energy to provide ED/EDE directed at the eyes for ocular health as a supplement and/or treatment for ocular health and ocular disease or injury. FIG. 3 illustrates utilizing a variation of the goggle 200' disclosed with respect to FIGS. 2A and 2D in which the device 500 is a goggle is fitted with light emitting diodes (LEDs) 502 affixed general to a light emission region 505 through the front wall 230. The LEDs hardware and module or mountings should be appropriate under National Fire Protection Association (NFPA) 70®, National Electric Code® (NEC) for use in Class 1 Division 1 settings as Hydrogen is known as an explosive gas. Larson electronics offers a variety of such complaint LED lighting systems and these general show the availability of such safe LED systems for use in class 1 division 1.

The LEDs illumination or energy produced is generally directed towards the users eyes 110. The LEDs are need not be set in a ring shape as shown but rather those of ordinary skill in the art will recognize that different spacing and placement of LEDs in any array or spacing which can direct the emitted light towards the eyes is within the scope of this disclosure. The LEDs are in signal communication with and driven by a controller 300' and also receive power from the power supply 520. The controller provides power to the LEDs to drive them to produce one or more preselected spectrums of light preferable in the long red and near IR regions. There may be a plurality of different LEDs within the device. Red may be called long red within a spectrum of >625 nms to <700 nms with peak wavelengths >640-670 nm and Near-Infrared typical ranges from >700 nms and <1400 nm (with typical peak wavelengths: 850 nm, 940 nm, 1064 nm) these have been shown to affect bio-physiological functions and are also described herein as "bioactive" they may improve eye health, skin health, hair growth, and cognitive function. The Emissions of Long Red and Near-Infrared are (RBL) are controlled by choice of LED, controlled voltage supplied to LEDs to drive or overdrive some LEDs in the device may produce long red and other produce near IR. One or more sensors or receivers 510 may be placed in or outside of the goggles which receive the LED emissions and via signal communications provide input 515 to the controller 300' of sampling regarding the amount of photonic energy supplied. Alternatively, or in addition to, a look up table (LUT) may be used to provide input to the controller regarding the light being generated by the LEDs based on the specific LED or LED module specifications and at least one of the LED driver voltage and current or whereby the different LED groups (red, long red and/or near IR) are controlled as to at least one of on/off, voltage and duration of on/off. These measurements and controls are used to provide an EDE. The system and controller may use PWM to control output and/or may use voltage to adjust the volume of photodynamic energy of a given spectrum over time.

Those of ordinary skill in the art or the skilled artisan will understand the disclosure to include light produced by a compliant laser instead of or in conjunction with an LED and such laser is within the scope of this disclosure and claimed hereby.

Figure 4:
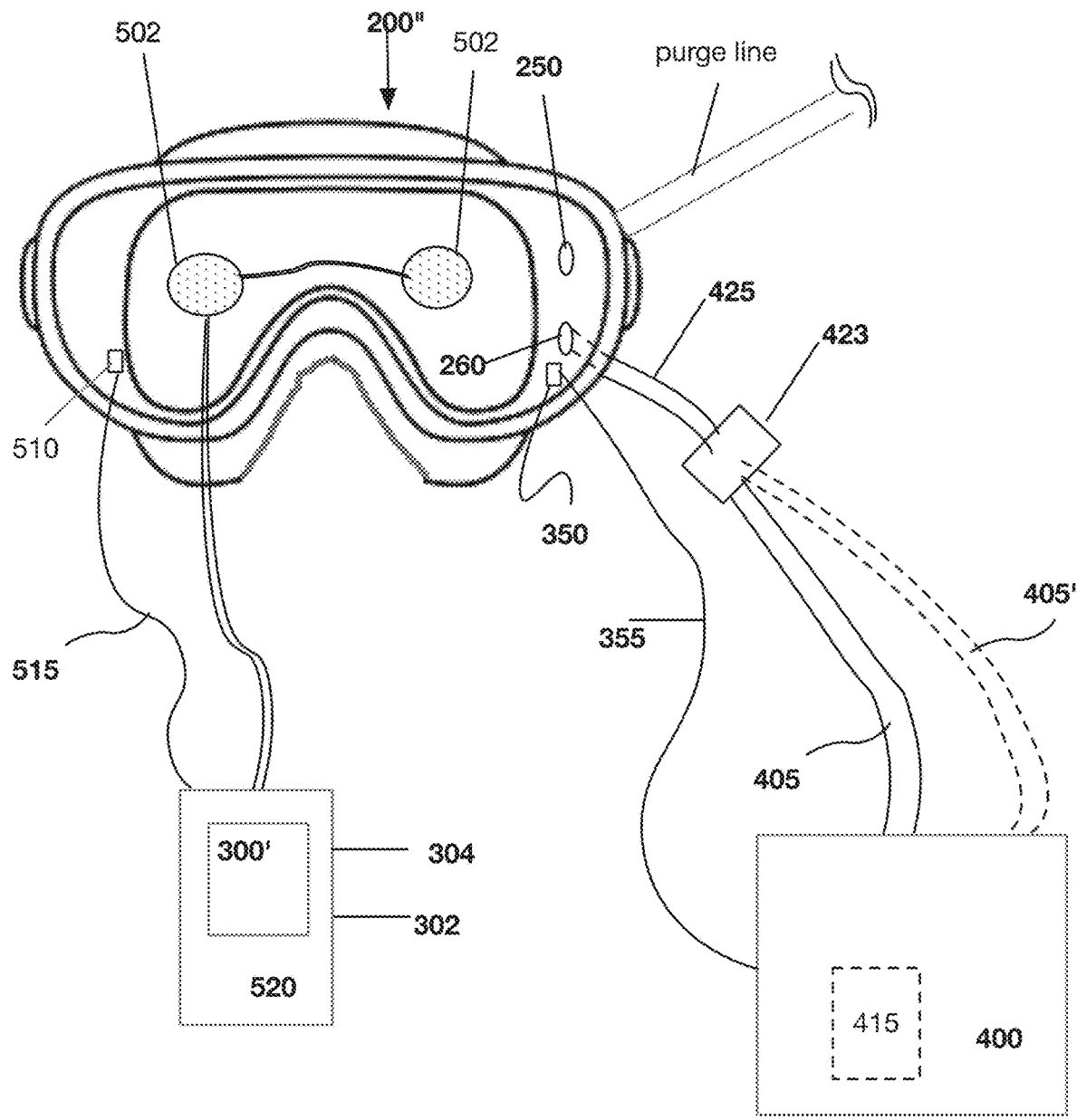
FIG. 4 is a representation of an energy and fluid delivery device to deliver aliquots of photodynamic energy and at least one fluid to the eyes of a subject.

FIG. 4 illustrates a system which both supplies one or more fluids to the eyes and supplies EDE of red light, near infra-red and/or long red in ED for eye supplementation, health and/or treatment. In this exemplar multiple controllers are illustrated (300 and 300') and multiple power supplies (520 and 415) however, those of ordinary skill in the art will recognize that a single controller is within the scope of this disclosure. Those of ordinary skill in the art will recognize that a single power supply is within the scope of this disclosure. Although aspects of the device and system illustrated in FIG. 2A are shown in FIG. 4 as part of that system, the device and system and aspects thereof illustrated in FIG. 2C are equally functionally and may be configured to work with the energy delivery systems and methods illustrated in FIG. 4.

In this exemplar a secondary fluid transport 405' is illustrated. Additional fluid transports allow the system to direct sequenced or purge fluids which may be supplied via separate storage vessels or pumps through separate supply lines. Those separate supply lines may intersect 423 to a common supply line 425 or they may fluidly connect to the goggle 200' individually.

Figure 5:
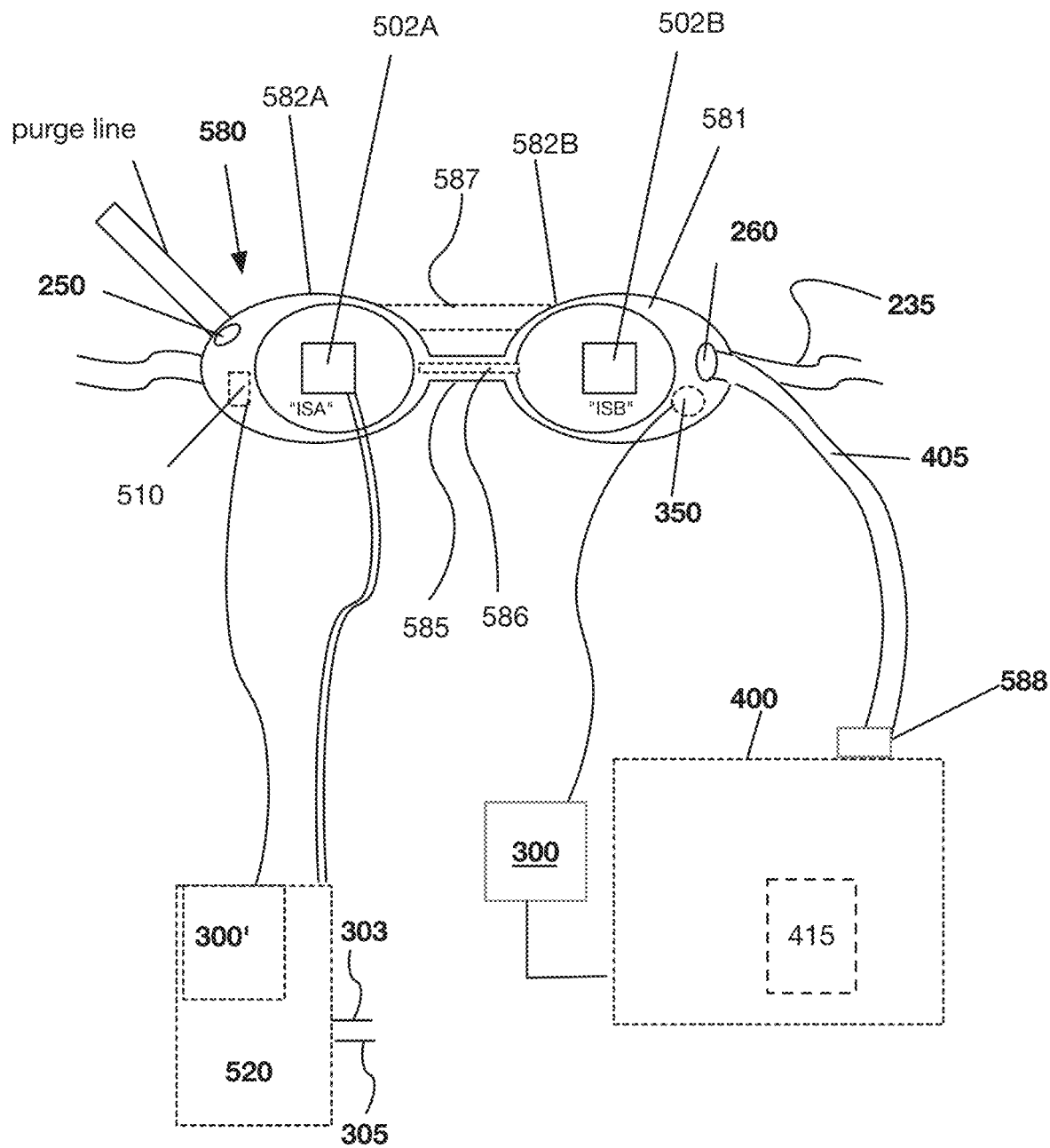
FIG. 5 is a representation of a low volume energy and fluid delivery device to deliver aliquots of photodynamic energy and at least one fluid to the eyes of a subject.

FIG. 5 illustrates a low volume system 580 which both supplies one or more fluids to the eyes and supplies EDE of red light, near infra-red and/or long red in ED for eye supplementation, health and/or treatment. LEDs and/or LED modules with LEDs that have nominal output in the red, long red or near IR spectrum are mounted on, or positioned to illuminate through the goggles 581 and direct illumination in the selected spectrum towards the eyes of a user. In this exemplar each eye is covered by a cup 582A and 582B each cup has an interior space or volume "ISA"/"ISB" preferable of less than 50 ml and more preferable of less than 30 mls. The cups are fluidly connected via an interconnect 585 wherein gaseous fluid can freely flow via a fluid passageway 586 between the cups. Alternatively, or additionally one or more fluid passages 587 may be used to connect the cups. It is also within the scope of this disclosure that the gaseous fluid is delivered directly to one or both cups with a fluid connection into that cup 582A and/or 582B. At least one purge line is connected to at least one relief valve 250. If cups are supplied gaseous fluid separately then each cup may have a fluid relief valve. Alternatively, or in addition a pressure sensor 588 may be configured to sample the pressure in the fluid transport hose 405 and said sampling is reported to the controller which is in signal communication with the pressure sensor. The controller uses such sampling data to stop the flow of gaseous fluid or continue same. Multiple controllers are illustrated (300 and 300') and multiple power supplies (520 and 415) however, those of ordinary skill in the art will recognize that a single controller is within the scope of this disclosure. Those of ordinary skill in the art will recognize that a single power supply is within the scope of this disclosure.

Figure 6:
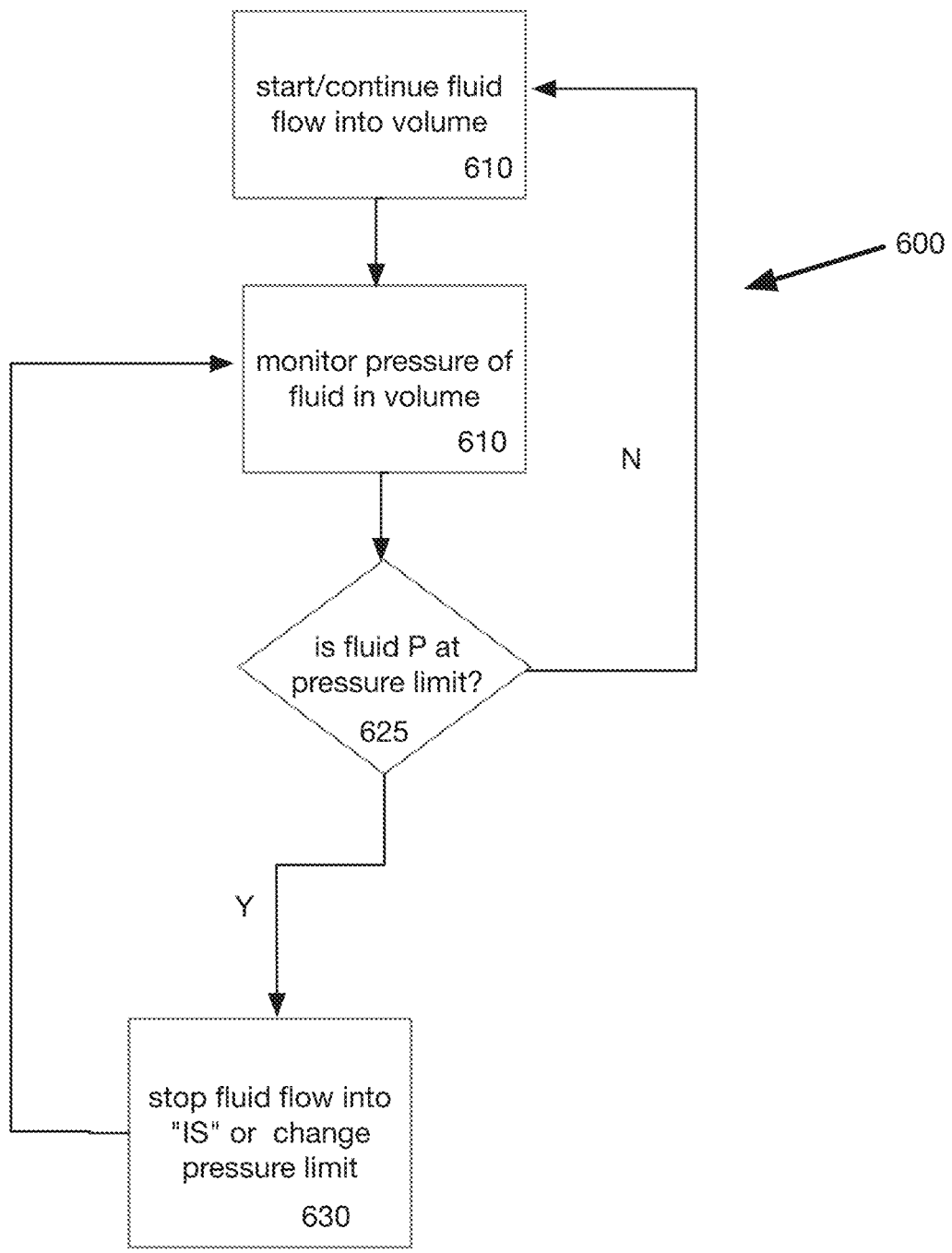
FIG. 6 is an operational flow diagram for fluid delivery.
Figure 7:
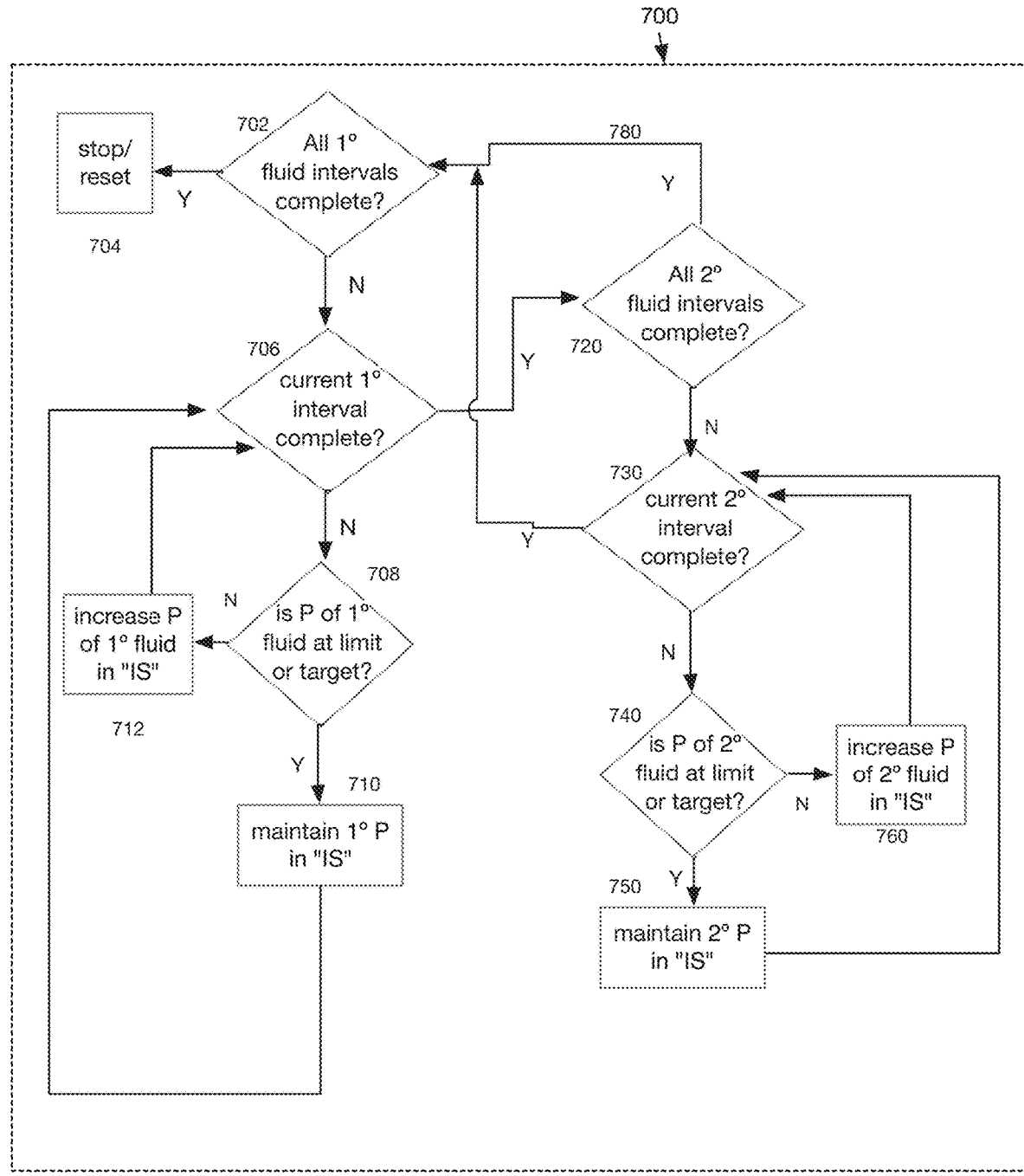
FIG. 7 is an operational flow diagram for sequenced first fluid delivery and a second fluid delivery.
Figure 8:
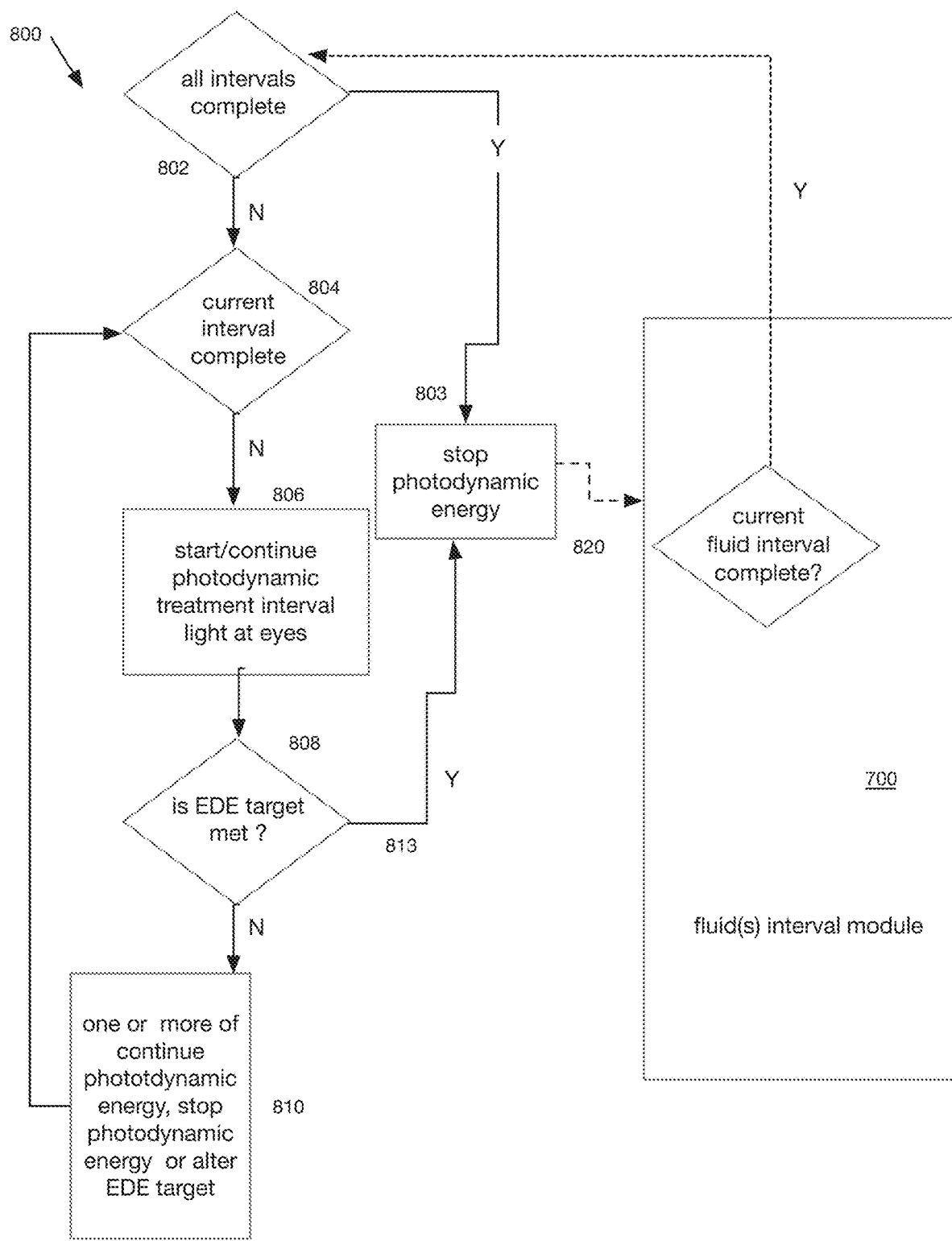
FIG. 8 is an operational flow diagram for fluid delivery interval(s) and delivery of EDE aliquots of photodynamic energy interval.
Figure 9A:
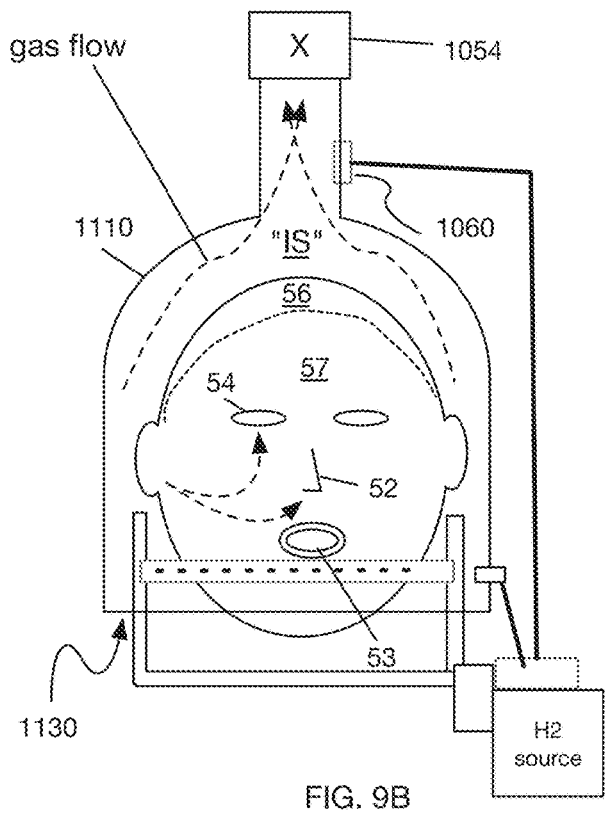
Figure 9A:
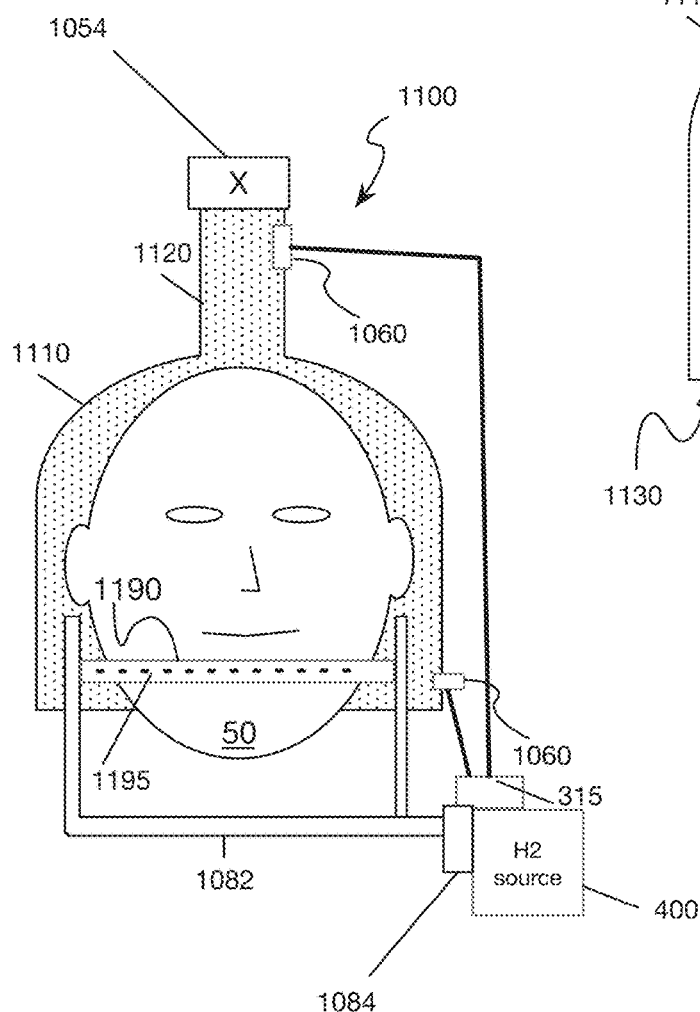

FIGS. 6-8 illustrate aspects of methods for delivering at least one of fluids and energy in selected or varied aliquots to the mammalian eye.

FIG. 6 is a simplified operational flow diagram showing aspects of fluid delivery to eyes for topical use. The fluid as previously noted may be oxygen, hydrogen, atmospheric air or oxyhydrogen. The system and method 600 need not be limited to delivering oxyhydrogen (HHO), rather the figures for simplicity do not list all possibilities. In this simplified flow diagram of a decision is made by the controller (300/300') to start or continue fluid flow 610. In this instance that fluid flow may be from a pressurized supply of gas. Said supply will have a pressure regular (not shown) to limit the pressure of the fluid which is being transported to the interior space to treat the eye. In other instances the fluid gas may be produced in more of an on demand fashion. That produced gaseous fluid also should be transported via a pressure regulated system to minimize pressure spikes.

A pressure monitor in the system measures the fluid pressure in the enclosed space "IS" 620. The controller decisions whether the fluid being supplied has achieved a target pressure inside the interior space 625. That value is acquired via at least one of the pressure of the fluid delivered from storage vessel or the pressure of gas produced via chemical action, the pressure is measure by a pressure sensor. If the controller decisions that the target pressure is met then the controller either stops the flow of oxyhydrogen into the volume or interior space or varies the pressure limit on the pressure relief means 630. If the target pressure is not met then the controller decisions whether to start or continue oxyhydrogen flow. The system samples at a rate in excess of every 50 milliseconds and more preferable above a rate of every 10 milliseconds.

FIG. 7 is an operational flow diagram of aspects of a fluid interval module which shows a sequenced first fluid delivery and a second fluid delivery. The overall system 700 is shown configured to deliver a primary and optionally a secondary fluid. However, those of ordinary skill in the art will recognize that additional fluids may be included in the sequence to extend the system to a "nth" fluid. The controller decides if the primary intervals have been completed. The system uses criteria such as a timer and decisions if all primary intervals are complete 702, if "yes" then the system stops or resets 704, if "no" the system determines if the current primary interval is complete 706. If "no" the system determines if the pressure at a target pressure or limit for the primary fluid has been met 708, if "yes" then the maintain pressure of primary fluid in IS 710. If "no" then increase pressure 712 of primary fluid in IS and continue to sample and check if primary interval is complete 706. When current primary interval is complete then determine if all secondary fluid intervals are complete 720 if no determine if current secondary interval is complete 730. If "no" then determine if pressure of fluid in IS for secondary interval is at target or limit 740, if "yes" maintain the pressure of secondary fluid in IS 750. If "no" then increase pressure of secondary fluid in IS 760. If all secondary intervals are complete 780 then check if all primary intervals are complete 702.

FIG. 8 is an operational flow diagram 800 of aspects of sequenced photodynamic treatment interval which optionally also is combined with one or more fluid delivery intervals as described in reference to FIG. 7. The controller determines if all photodynamic intervals are completed 802 if "yes" then the system stops the photodynamic treatment (or resets) 803 and optionally 820 starts the fluid interval module 700. If "no" the system determines if the current photodynamic treatment interval is complete 804. If "no" the system continues or starts a photodynamic treatment interval 806 and then determines if the EDE target is met 808. If the target is not net then the system one or more of continue photodynamic energy, stops photodynamic energy or alters EDE target 810. The system then continues to monitor/sample if the current interval is met. If the EDE target 808 was met then the system will stop the photodynamic energy 803 and optionally 820 check status and/or start the fluid interval module 700. When the fluid interval module is complete the controller will check if all photodynamic intervals are complete 802.

FIGS. 9A-11 show a series of exemplary implementation wherein an enclosure covers at least the eyes 54, nose 52, mouth 53, hairline 56, face 57 and head 50 may be covered. Providing dosing or aliquots of hydrogen gas and/or HHO (oxyhydrogen) has been shown to reduce ROS. Disclosed is both the local application of the gaseous fluid to eyes and hairline and inhalation of hydrogen as a pulmonary fluid. Reduction in ROS is associated with cardiovascular improvements, eye health, skin health and air follicle health. Electrolytically generated hydrogen warm water cleanses the keratin-plug-clogged hair-pores and promotes the capillary blood-streams, more markedly than normal warm water does".

One exemplary system 1100 covering the head 50 of a subject may optionally have hydrogen sensors 1060 configured to measure hydrogen within the enclosure and which may provide data to a controller which is configured, or has software configured, to maintain a selected parts per million ppm) of a selected gas. The enclosure has a body 1110 fluidly connected to a vent 1120 and an may have an open bottom 1130 to allow atmospheric air to pass in. A flow restrictive valve 1054 may be added at the end of the vent to control gaseous fluid flow out of the enclosure. Said vent in some instances may be connected to a source of negative pressure (not shown). A source of hydrogen 400 which may be a tank, a generator or the like is fluidly connected 1082 to a distributor 1190 which provides one or more apertures 1195 to disperse gaseous fluid. The fluid connection 1082 may be controlled by a flow restricting means such as a valve 1084 to control the pressure and quantity of gaseous fluid delivered. The valve may be controlled by a controller 315. The controller may receive input from optional pressure sensors 1060 to adjust the gaseous fluid flow. The enclosure provides for gaseous inhalation and local application to at least one of the user's eyes 54, nose 52, mouth 53, hairline 56, face 57 and head 50

FIGS. 10A and 10B illustrate another exemplar of an enclosure with aperture for dispensing fluid containing hydrogen 1200. The enclosure 1201 has an inner surface 1202 and has a distributor 1190 encircling the open bottom. A rigid or semi-rigid distributor can have the additional function of keeping the enclosure open. The gaseous fluid containing hydrogen is connected via an interface 1204 to the enclosure and a valve 1084 may be used to control gaseous flow therein. In some instances the system receives a gaseous fluid which upon exiting the aperture(s) 1095 baths the eyes and may be inhaled. The aperture(s) is direct into the inside of the enclosure. The gaseous fluid also will bath the skin and hair. Hydrogen at concentrations of about 3% and above have been shown to reduce oxidative stress in mammalian systems. At least one study equates hydrogen supplementation to reduced depression and anxiety. FIG. 11 illustrates another exemplar of an enclosure with aperture for dispensing fluid containing hydrogen 1300. a shaped opening 1302 is configured to not enclose the user's nose and mouth. The aperture 1095 is configured to disperse gaseous fluid in a predetermined region inside the enclosure. As noted above the sensors may be used to control gaseous flow in response to measurements via the controller.

Supplementation of vision to slow decline and/or reduce of vision losses during the ageing process can ameliorate cognitive decline related to loss of vision.

Disclosed herein are methodologies and therapies including but not limited to light therapy (photodynamic), localized hyperthermia and chemical. The therapies may be combined or applied separately to treat hearing loss in mammals and more specifically to treat tinnitus.

FIGS. 12A through 20B disclose nonlimiting aspects of compositions and devices as well as control systems and compliance schema. The compositions herein can be included in a pharmaceutical or nutraceutical composition together with additional active agents, carriers, vehicles, excipients, or auxiliary agents identifiable by a person skilled in the art upon reading of the present disclosure, and such compositions are within the scope of this disclosure. All publications cited herein are hereby incorporated by reference as if fully set forth herein.

The compositions disclosed herein can be included in a pharmaceutical or nutraceutical composition together with additional active agents, carriers, vehicles, excipients, or auxiliary agents identifiable by a person skilled in the art upon reading of the present disclosure, and such compositions are within the scope of this disclosure. All publications cited herein are hereby incorporated by reference as if fully set forth herein.

The pharmaceutical or nutraceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds and/or adjuvants can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol, terpenes, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

In some instances a mammalian a subject to is supplemented via application of intravenously (IV) administered of gelatin with a 1000 ml Infusion solution including: Gelatin-polysuccinat 40,00 g (Mw 30 000, Mn 23 200) Electrolyte: Natrium 154 mmol/l (35 mg/l) Chloride 120 mmol/l, 1000 ml 154 mmol sodium as sodium chloride. along long with between 7.5 and 15 grams of vitamin C in at least 250 cc of saline. The may be administered before or during application of the EDE. If a topical agent (as disclosed herein) is applied, the topical agent may be applied prior to the application of the EDE.

FIG. 12A is an overview of gross anatomy of an ear 1500 having an outer ear 1505. The ear canal "EC" is a pathway to the cochlea 1600 which is a tiny, snail-shaped structure. It is the main organ of hearing and is part of the inner ear. Cochlear damage means that all or part of your inner ear has been hurt. Damage to the cochlea typically causes permanent hearing loss. This is called sensorineural hearing loss (SNHL). Many things can cause SNHL, or cochlear damage, including loud or extended noise exposure, certain powerful antibiotics, meningitis, Meniere's disease, acoustic tumors, and even the natural decline in age can cause hearing loss.

Noise-induced hearing loss, or NIHL, occurs when your ears are exposed to overly loud sounds. Any sound over 85 decibels is considered to be dangerous to the ears and your hearing. The louder the sound, the shorter the length of time that is considered "safe" exposure. For example, at a loud rock concert, sound may reach 115 decibels, and only a short 15 minutes can cause cochlear damage. In addition, repeated exposure to loud sounds can cause additional cochlear damage. The only way to prevent noise induced hearing loss is to limit exposure to loud sounds and wear ear protection.

Shown in FIGS. 12A-14 are aspects of energy delivery devices 1600 used with methods, and devices disclosed herein to deliver at least one of a supplement, adjuvant and/or EDE to the ear canal "EC" of a user 1510 and more specifically to the tissue surrounding the cochlea 1700. The device 1600 is connected to a power supply via a PCB (see FIG. 15), and is controlled via a microprocessor controller 2000. The energy is delivered as at least one of bioactive light such as RBL and blue light or as a localized heat via IR light to heat tissue in the ear surrounding the energy deliver device 1600. LEDs or lasers 1610 are effective devices as the may be tailored to have narrow beam angles 1615 when outputting energy.

Shown in FIGS. 13 and 14 show a device which incorporates energy delivery device(s) as described herein with a wearable system 1800. The wearable system is at least one of self contained and powered via batteries or it may be a wired system that required wall outlet power and is not as portable. At least one ear covering 1810 is placed over the outer ear 1505. The ear covering may be attached to a support member 1812. There may be bilateral ear coverings connected to the same support member. Within the ear covering is a chamber 1818 formed to at least one of position the energy delivery device 1600 and position one or more sensor 1620 and reflect scattered or reflected energy via a parabolic reflector back into the ear canal "EC". The LED or laser will either have an integrated lens to produce a fixed beam angle 1900 or one or more lenses, diffusers or light shaping filters may be added to achieve beam contouring. Such beam shaping systems and materials are known in the art and those of ordinary skill in the art will recognize that this disclosure teaches directing energy into the ear canal and using known devices to focus or direct such energy is within the scope of this disclosure. The PCB and power supply 1815 are shown attached to an ear covering Moreover, in addition to using a red or long red mode to encourage vasodilation and NO production disclosed is a device also having a blue light mode which generates circadian stimulating energy and the ability to shift from a first mode to a second mode allows for both treatment and protection of hearing (visa vie ameliorating the effect of loud noise exposure (such as loud music or explosions)) and production of circadian stimulating blue light in an EDE to combat SAD and/or generally enhance at least one of memory, focus and concentration levels in subjects ID. Bright light therapy has been studied in association with ear canals but was a gross application of bright full spectrum light. However some positive early results were obtained in a limited study. (See Jurvelin H, Takala T, Nissila J, et al. Transcranial bright light treatment via the ear canals in seasonal affective disorder: a randomized, double-blind dose-response study. *BMC Psychiatry.* 2014; 14:288. Published Oct. 21, 2014).

The energy deliver LED or lasers are envisioned as one or more at preselected wavelengths. RBL and blue light as well as IR (for heat generation) for example which penetrate the ear. The photodynamic aspects cause at least increased NO is helpful for vasodilation and to allow greater blood flow into the cochlear microvasculature. The system may be operated in multiple modes wherein the LEDs or lasers may simultaneously or sequentially provide specific wavelengths of light such as shifting from circadian stimulating blue (first mode) to RBL (second mode) and/or also to a third warming or heat mode. In addition an input device (not shown) such as a smart phone or tactile pad can be used by to communicate with the controller and increase or decrease any one of the heat and bioactive light corresponding to one of comfort and level of tinnitus (ringing).

Figure 15:
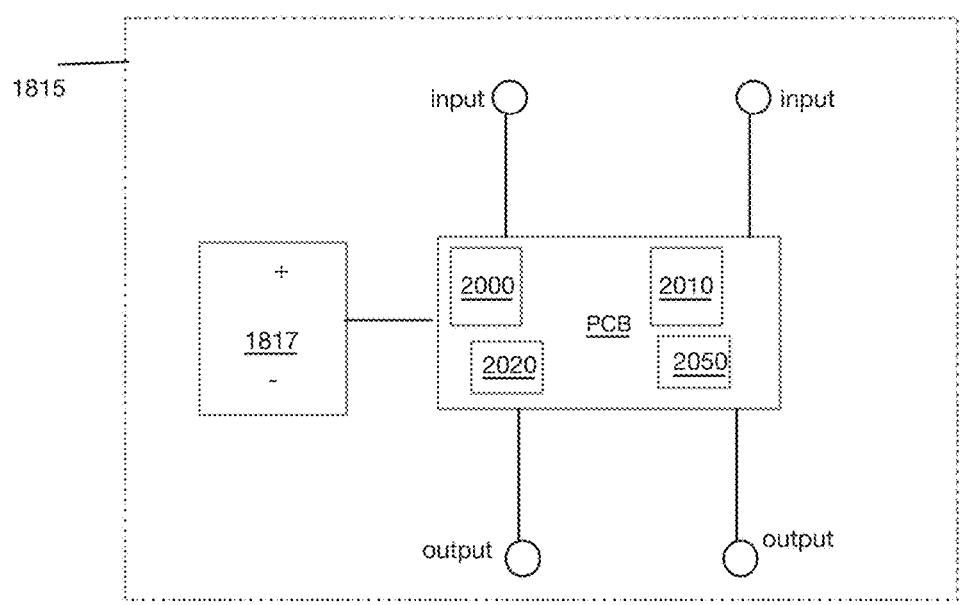
FIG. 15 shows aspects of an electrical control and power system of the disclosed wearable energy delivery and feedback device of the disclosure.

FIG. 15 shows aspects of basic elements of a control module 1815 with a PCB and power supply 1817 including but not limited to inputs and outputs which may include inputs from sensors and outputs to the energy providing devices. A microprocessor 2000 controller is used in conjunction with a controller 2010, which may include PWM control. On the PCB there is memory 2020. Preferably a wireless protocol chip set 2050 with antennae is included to allow communication and/or data transfer from the device to servers (see FIG. 17) which may be through a network.

Figure 16:
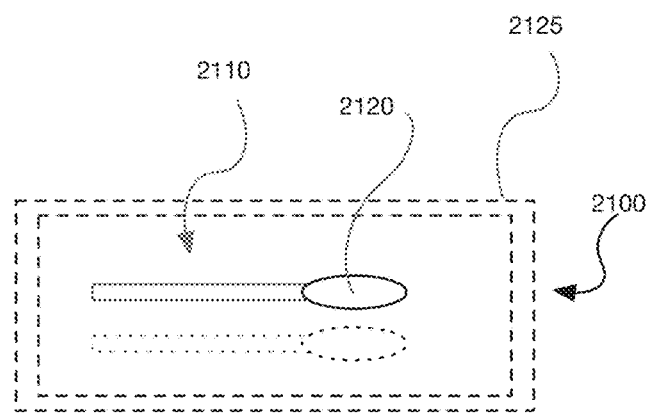
FIG. 16 is an overview of a device to deliver prepackaged topical localized doses of therapeutic agent and/or adjuvants of the disclosure.

FIG. 16 shows a disposable delivery package 2100 wherein a barrier 2125 contains a swab 2110 having a wet end 2120 which is contains a predetermined single use dosage of DMSO (or other agent that is used in dermal deliver) and at least one of a vasodilator and a TNF-α inhibitor (such as Etanercept). In Tinnitus we have found that both vasodilation and inhibition of TNF-α show improvements in reducing the symptomology of tinnitus. Etanercept is extremely expensive and by applying it locally with DMSO very small aliquots of the Etanercept may form an effective dose for localized TNF-α inhibition.

Figure 17:
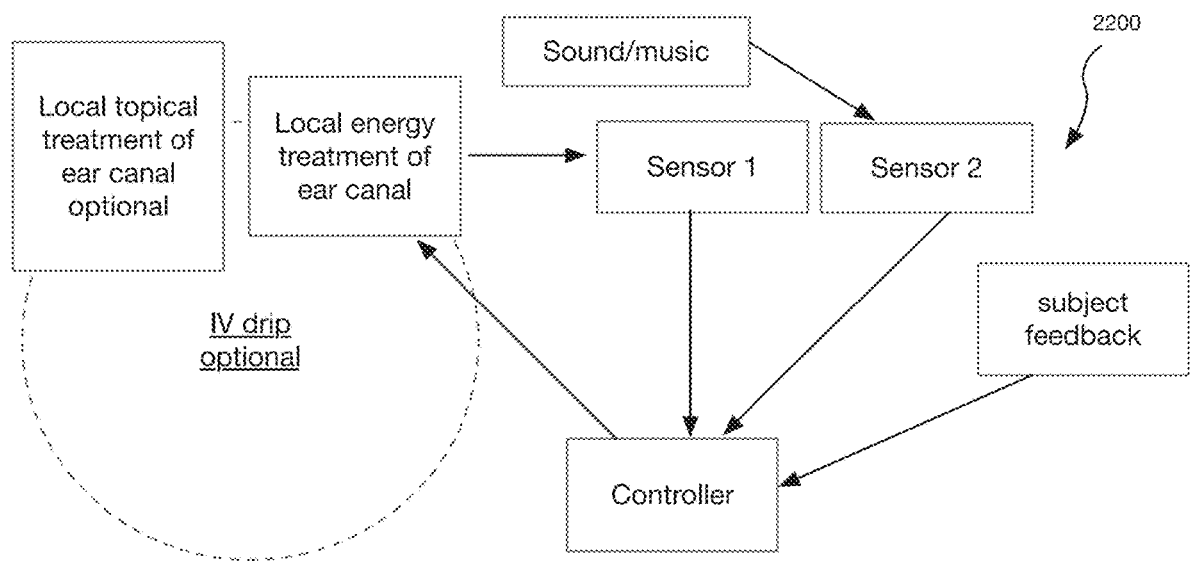
FIG. 17 is a flow diagram of aspects of the operation of a device and method to deliver controlled aliquots of energy to a user and to receive feedback device of the disclosure.
Figure 18:
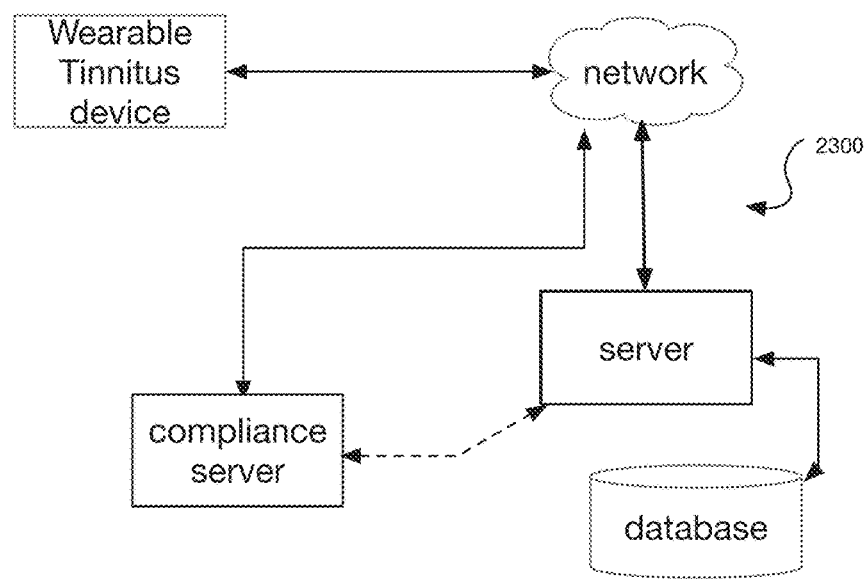
FIG. 18 is a flow diagram of aspects of a compliance, use and monitoring method to receive use data and evaluate treatment compliance.

FIG. 17 is an overview of the portion of the method of supplementation which may include combinatorial supplements for the energy delivery device. delivery of the light supplement in an EDE or ECE is protective of cochlear microvasculature it also may separately be applied to adjust circadian cycles (sleep), increase memory and concentration if may also be combined with topical supplement non gaseous fluid.

A first sensor or group of sensors measures a condition in the ear canal such as temperature, pressure, O2 saturation, reflective light and is an input to the controller wherein according to presets or dynamic adjustment. A second sensor or group of sensors measures decibels, vibration of the ear canal structure, frequency and/or duration of sound or noise. For example, if the user is playing music at a level which exceeds a threshold the device is configured to dynamically adjust the EDE to a level to support cochlear microvascular health when noise stress is directed at the cochlea. A time clock in the controller may also adjust circadian stimulating (blue) lighting in the ear canal or red, long red and near IR (BRL) in the ear canal to reset or support healthy circadian cycles. Patient/user/subject feedback to the controller from known methods which include but are not limited to spoken commands, touch pad, computing device Apps and the like can also be used to supply subject feedback for additional adjustment of the system.

The intravenously (IV) administered compound include gelatin with a 1000 ml infusion solution included: Gelatin-polysuccinat 40,00 g (Mw 30 000, Mn 23 200) Electrolyte: Natrium 154 mmol/l (3535 mg/l) Chloride 120 mmol/l, 1000 ml 154 mmol sodium as sodium chloride. Along with between 7.5 and 15 grams of vitamin C in at least 250 cc of saline. The may be administered before or during application of the EDE. If a topical agent (as disclosed herein) is applied, the topical agent may be applied prior to the application of the EDE. One or more sensors may supply data such as O2 levels and temperature within at least one ear covering. That data is processed by the controller and used to adjust the energy delivered.

Compliance and monitoring compliance is often a challenge. Accordingly, in some instances the a Wearable Tinnitus Device (WTD) (see FIG. 13) may be operated generally under the protocol 2300 set forth in FIG. 18. The Wearable Tinnitus Device (WTD) is placed in signal communication with a network. The network communicates with a server and provides data either from memory stored on the WTD (as described previously) or real time use data. Data may include time of use, duration of use, date of use, any user feedback adjustments and the like. The server is in signal communication with a server. The network or the Server may also communicate with a compliance server wherein records of use by the user may be maintained. Such records are critical to agglomerate to determine if the user (if use is remote from a treatment provider) is actually using the device for sufficient time and regularly and how that use corresponds to level of discomfort The data which may be transmitted is at least all data described within.

Figure 19A:
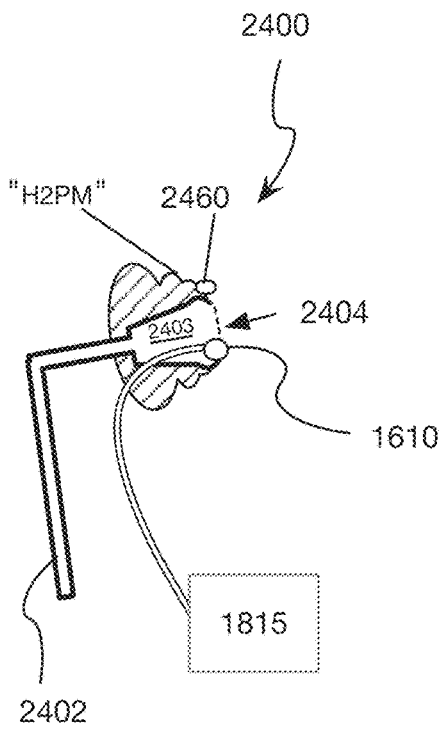
FIG. 19A shows a partial cut-away view of a wearable energy and fluid delivery device of the disclosure.
Figure 19B:
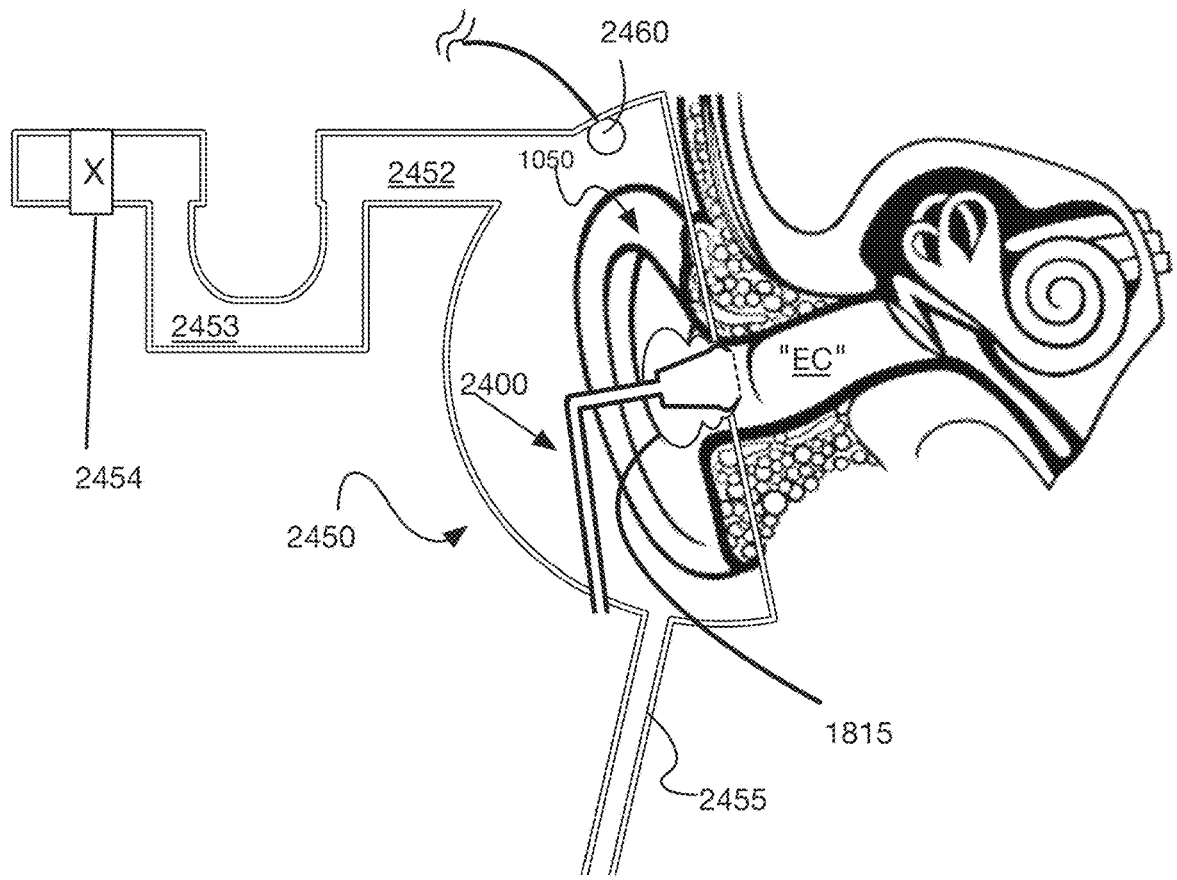
FIG. 19B shows the device of FIG. 19A as part of a method of delivering energy and fluid to the ear canal.

Shown in FIGS. 19A and 19B are aspects of energy and fluid delivery device 2400 used with methods, therapies and devices disclosed herein to deliver at least an adjuvant and/or EDE to the tissue surrounding the cochlea 1500. The device 2400 is connected to a power supply via a PCB 1815 and is controlled via a microprocessor controller 2000. The energy is delivered as at least one of bioactive light such as RBL and blue light or as a localized heat via IR light to heat tissue in the ear surrounding the energy deliver device 2400. LEDs or lasers are effective devices as the may be tailored to have narrow beam angles when outputting energy.

The wearable system 2400 is at least one of self-contained. In its simplest iteration the equivalent of an in-ear headphone or "earbud" is the ear canal "EC". A hydrogen permeable outer shell "H2PM" forms a cavity 2403 which is fluidly connected 2402 to a source for at least on of oxyhydrogen fluid and hydrogen fluid and provides a fluid pathway through an end nozzle or aperture 2404 to form a passageway for hydrogen or oxyhydrogen to pass into the ear canal. The hydrogen permeable outer shell or permeable membrane H2PM is configured to position the device in the ear canal to support gaseous fluid flow and to at least one of release from any seal formed seal with the ear canal and allow gaseous fluid above a preselected pressure in the ear canal to vent out of the ear canal. In some optional instances, a hydrogen sensor 2460 in signal communication with a controller whereby the quantity of gaseous hydrogen measured may be used at the controller to adjust the flow of hydrogen of oxyhydrogen to the device. In some optional instances the device and method may also include the aforementioned means to deliver aliquots of energy via LEDs or lasers 1610 powered via batteries or it may be a wired system that required wall outlet power and is not as portable. In some instances a collection cover 2450 may be placed over the ear whereby gaseous fluid exiting the ear canal may be vented through a fluid connection 2452 and a hydrogen sensor 2460 in signal communication with a controller whereby the quantity of gaseous hydrogen measured may be used at the controller to increase or decrease the flow of hydrogen of oxyhydrogen to the device may be measured in the collection cover 2450. Said collection cover provides a pathway to direct the spent hydrogen gas or spent oxyhydrogen for disposal.

In other instances an optional inlet 2455 for gaseous fluid such as hydrogen or oxyhydrogen may directly feed gaseous fluid into the collection cover 2452. In this exemplar the wearable system may be removed and the gaseous fluid supply to the ear canal is provided via the collection cover via the input 2455 and the collection cover is configured to partially seal around the ear. The fluid collection may have a trap 2453 whereby the lighter than air hydrogen will only flow out of the device when it fills the trap. Alternatively a one way valve 2454 may be configured to allow passage of gaseous fluid above a predetermined pressure. In some optional instances, a hydrogen sensor 2460 in signal communication with a controller whereby the quantity of gaseous hydrogen measured may be used at the controller to adjust the flow of hydrogen of oxyhydrogen to the device.

Figures 20A, 20B:
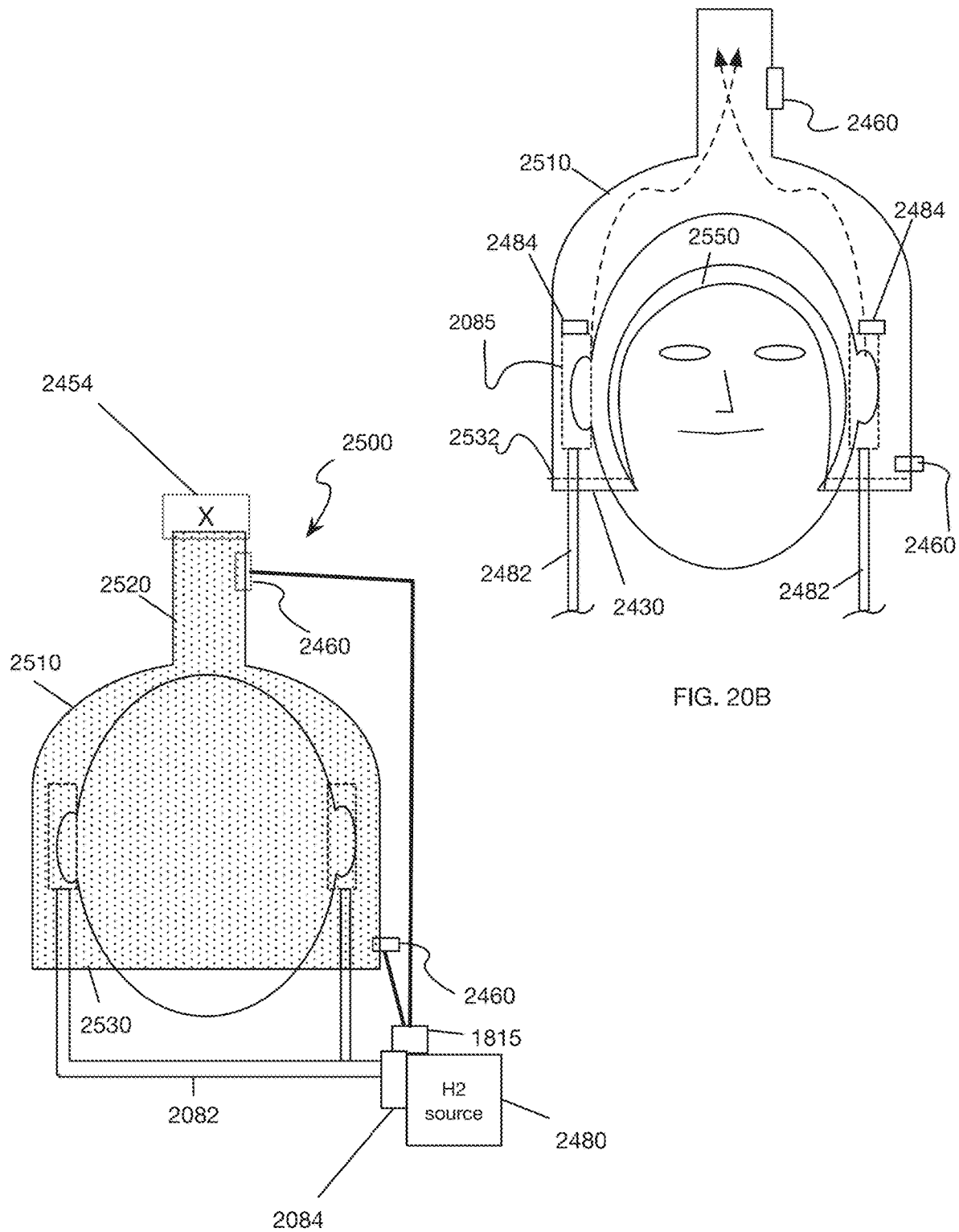
FIGS. 20A and 20B show a low pressure gaseous fluid delivery and collection system.

FIGS. 20A-20B show a series of exemplary implementation wherein an enclosure covers the ears 2450 of the subject.

This disclosure provides novel devices, systems and methods to bath the ears and inner ear structure with hydrogen rich gaseous fluid, this is a local application which does not require digestion of water laced with hydrogen or inhalation of hydrogen gas. Hydrogen aliquots are supplied to and permeate the tissues and structures.

Age-related hearing loss (ARHL) or presbycusis is the third most prevalent chronic disease among older adults. It can vary in severity from mild to severe, the more severe forms affecting communication and contributing to social isolation, depression, and possibly dementia. A recent study exposed an animal model to high levels of H2O2 and it has been shown that the H2O2-exposed cochlear cells exhibited several additional senescence-associated properties, including high senescence associated β-galactosidase activity mainly in sensory hair cells, together with increased levels of p21, p38, and p-p38. The in vivo results show senescence-accelerated premature cochlear aging. Mitigation of ROS on H2O2-induced DNA damage and senescence-like phenotype, with 10 μM EUK-207, a potent synthetic superoxide dismutase/catalase mimetic that scavenges superoxide and hydrogen peroxide and the study reported that (i) ROS is connected to age-related sensory hair cell degeneration, (ii) ROS-induced DDR driving senescence-like features may account for premature cochlear aging, and (iii) pharmacological scavenging of superoxide and hydrogen peroxide can mitigate Hydrogen inhalation and hydrogen infused water has been shown in animal models to have some ROS mitigation.

Hydrogen has been shown to have no adverse effects and great efficacy on nearly all pathogenic states involved in oxidative stress and inflammation One exemplary system 2500 covering the head of a subject may optionally have hydrogen sensors 2460 configured to measure hydrogen within the enclosure. The enclosure has a body 2510 fluidly connected to a vent 2520 and an may have a partially opened bottom 2530 to allow atmospheric air to pass in a flow restrictive valve 2454 may be added at the end of the vent to control gaseous fluid flow out of the enclosure. Said vent in some instances may be connected to a source of negative pressure (not shown). A source of hydrogen 2480 which may be a tank, a membrane electrolyzer, a generator or the like is fluidly connected 2482 to ear covering 2485. The hydrogen source specifically includes but is not limited to a source for oxyhydrogen (HHO) such as a generator or tank storage. The connection may be controlled by a flow restricting means such as a valve 2484 to control the pressure and quantity of gaseous fluid delivered. The valve may be controlled by a controller 1815. The controller may receive input from optional pressure sensors 2460 to adjust the gaseous fluid flow. In some instance the bottom edge 2530 is at least partially sealed along the line of 2432. The front of the enclosure shown in FIG. 20B is temporarily sealed against the face of the user via an interface 2550.

The ear coverings are configured to cover the outer ear and direct gaseous flow into the ear canal. The ear covering does not need to seal over the ears. The coverings may also be permeable to hydrogen at at least one of a predetermined rate and pressure to allow hydrogen to pass therethrough. In some instances a valve or flow control means 2484 may be in fluid connection with the ear covering whereby gaseous fluid within the ear covering may be controllable released into the enclosure.

Protection of, restoration of and/or reduction of hearing losses during the ageing process can ameliorate cognitive decline related to loss of hearing.

The invention claimed is:

1. A method to deliver therapeutically effective treatment for relief of tinnitus, the method comprising:
   directing at least one effective dose or aliquot of light energy into an ear canal;
   said dose configured to produce heat in the ear canal;
   providing one or more temperature sensors configured to be in thermal communication with the ear canal and configured to be in signal communication with a control module;
   wherein the control module receives a user's selected comfort level input to limit heat in the ear canal;
   wherein the control module receives temperature sensor input and controls outputs of energy to limit heat in the ear canal;
   wherein said effective dose one or more of increases circulation in the cochlea vasculature, increases vasodilation in the cochlear microvasculature and increases nitric oxide in the local area adjacent to the cochlea.

2. The method of claim 1 wherein the light energy is at least one of red light, long red light, near IR light and blue light.

3. The method of claim 1 wherein the light energy is delivered via sequential modes adjusted by a controller.

4. The method of claim 3 wherein one or more additional sensors provide input to the control module for adjustment of mode, frequency, duration and intensity of said light energy.

5. The method of claim 3 wherein a first mode includes at least light energy with peak wavelengths of 850, 940 and 1064 nms and a second mode includes light energy with a peak of above 640 nm and below 700 nms.

6. The method of claim 1 the method further comprising apply an effective dose of gaseous hydrogen to the ear canal one of before, during and after applying the light energy.

7. The method of claim 1 whereby symptoms of tinnitus are reduced.

* * * * *